United States Patent [19]

Ross et al.

[11] Patent Number: 4,576,939

[45] Date of Patent: Mar. 18, 1986

[54] PENEM DERIVATIVES

[75] Inventors: Barry C. Ross, Luton; Graham Johnson, Milton Keynes, both of United Kingdom

[73] Assignee: Hoechst AG, Frankfurt am Main, Fed. Rep. of Germany

[21] Appl. No.: 439,898

[22] Filed: Nov. 8, 1982

Related U.S. Application Data

[63] Continuation of Ser. No. 217,819, Dec. 18, 1980, abandoned.

[30] Foreign Application Priority Data

Dec. 20, 1979 [GB] United Kingdom ................ 7943995

[51] Int. Cl.[4] .................. A61K 31/415; C07D 487/04
[52] U.S. Cl. .............................. 514/210; 260/245.2 R
[58] Field of Search ................ 260/245.2 R; 424/270; 514/210

[56] References Cited

U.S. PATENT DOCUMENTS

| | | | |
|---|---|---|---|
| 4,207,323 | 6/1980 | Beattie et al. | 424/270 |
| 4,290,948 | 9/1981 | Brain et al. | 260/245.2 R |
| 4,331,676 | 5/1982 | Gosteli et al. | 424/270 |
| 4,431,658 | 2/1984 | Afonso et al. | 424/273 R |

FOREIGN PATENT DOCUMENTS 1377715 12/1974 United Kingdom .
1455016 11/1976 United Kingdom .

Primary Examiner—Nicholas S. Rizzo
Attorney, Agent, or Firm—Curtis, Morris & Safford

[57] ABSTRACT

What are disclosed are penem compounds of the formula

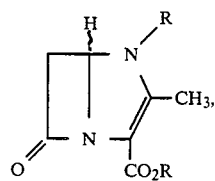

wherein R is hydrogen, a cation, or an esterifying group and $R^1$ is alkyl or aryl, methods for making such compounds, methods for using the compounds as a $\beta$-lactamase inhibitor or as an antibacterial agent, and pharmaceutical preparations containing the compounds.

10 Claims, No Drawings

PENEM DERIVATIVES

This is a continuation of application Ser. No. 217,819, filed Dec. 18, 1980, abandoned.

This invention relates to penem derivatives, to a process for their preparation, to pharmaceutical preparations comprising them, and to intermediates for use in the preparation of substances having antibacterial activity and/or β-lactamase inhibitory and/or inactivating activity.

The term "penem" is used herein to denote the following structure

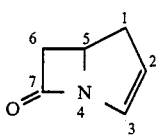

Penems and derivatives thereof substituted in various ways at any one or more of positions 2,3 and 6 have been proposed previously, as have certain analogues in which the carbon atom at position 1 has been replaced by an oxygen atom (oxapenems, see, for example, Belgium Patent Specification No. 858515), or by a sulphur atom (thiapenems, see, for example, Belgian Patent Specification Nos. 849118 and 866845 and published European application 636).

The present invention provides a penem derivative of the general formula I

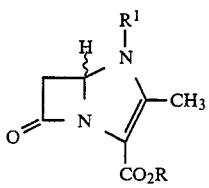

wherein $R^1$ denotes an unsubstituted or substituted straight or branched chain aliphatic group bonded to the ring nitrogen atom, or an unsubstituted or substituted aryl group; and R denotes a hydrogen atom, a cation or a carboxyl esterifying group.

A compound of formula I may have the R or S configuration at position 5 i.e. a compound may be 5R or 5S. The stereochemistry is preferably that found in naturally occurring penicillins.

The present invention accordingly includes any of the various possible isomers of the compound of formula I, in pure form or in admixture with any one or more other isomer(s). If desired, a mixture of isomers may be separated by a known method.

An aliphatic group $R^1$ may have up to 18 carbon atoms, for example, up to 12 carbon atoms, preferably up to 8 carbon atoms and especially up to 4 carbon atoms. An aliphatic group $R^1$ may be a straight or branched chain alkyl, alkenyl or alkynyl group.

An aryl group $R^1$ may comprise up to 12 carbon atoms and may also comprise two or more fused rings. An aryl group $R^1$ is preferably an unsubstituted or substituted phenyl group.

A group $R^1$ may be substituted, as appropriate and as desired, by one or more substituents, which may be the same or different. Examples of substituents are halogen atoms; oxo groups; hydroxyl and mercapto groups, alkoxy and alkylthio groups; alkylcarbonyl groups; carboxy, alkoxycarbonyl and alkylthiocarbonyl groups; alkanoyloxy and alkanoylthio groups; carbamoyl and carbamoyloxy groups, and carbamoyl and carbamoyloxy groups substituted on the nitrogen atom by one or two groups selected from alkyl and aryl groups, and the corresponding unsubstituted and substituted groups in which the oxygen atom or, each or either oxygen atom is replaced by a sulphur atom; nitro, cyano and azido groups; amido and imido groups; imino, amino, mono- and di-alkylamino, mono- and di-arylamino groups, and N,N-alkylarylamino groups; acylamino groups; sulphinyl, sulphonyl and sulphonamido groups; cycloalkyl groups; aryl, aryloxy, arylthio, aryloxycarbonyl, arylthiocarbonyl, arylcarbonyloxyl, arylcarbonylthio, aralkoxycarbonyl, aralkylthiocarbonyl, aralkylcarbonyloxy, aralkylcarbonylthio, aralkoxy, and aralkylthio groups; aromatic and non-aromatic heterocyclic groups, for example, having one or more heteroatoms, for example, up to 4 hetero atoms, which may be the same or different, selected from nitogen, oxygen and sulphur atoms, and preferably up to 14 atoms in total, and the corresponding heterocyclicoxy groups and heterocyclicthio groups.

Examples of aromatic heterocyclic groups are 1-methylimidazol-2-yl, 1,3-thiazol-2-yl, 1,3,4-thiadiazol-2-yl, 1,3,4,5-thiatriazol-2-yl, 1,3-oxazol-2-yl, 1,3,4,5-oxatriazol-2-yl, 1,3,4,5-tetrazol-2-yl, 2-quinolyl, 1-methylbenzimidazol-2-yl, benzoxazol-2-yl and benzthiazol-2-yl groups, and the corresponding 2-yl-oxy and 2-yl-thio groups.

Any substituent of $R^1$ that is itself capable of substitution may be substituted, for example, by any one or more of the substituents described above. Alkyl groups are preferably lower alkyl groups and aryl groups are especially phenyl groups.

The term "lower" as used herein denotes a molecule, group or radical having up to 8 carbon atoms, and especially up to 4 carbon atoms. Unless stated otherwise, halogen atoms are fluorine, chlorine, bromine and iodine atoms. The term "known" means in actual use in the art or described in the literature of the art.

$R^1$ preferably represents a methyl, ethyl, n-propyl, iso-propyl, n-butyl, sec-butyl, iso-butyl or tert-butyl group;

a —CH₂aryl group;

a —CH₂COOR⁵ group, in which R⁵ represents hydrogen or a carboxyl esterifying group R as defined hereinafter, a —CH₂CONR'R" group, in which R' and R", which may be the same or different, each represents a hydrogen atom, an alkyl group or an aryl group, or R', R" and the nitrogen atom together form a ring; or an unsubstituted phenyl group or a phenyl group substituted by one or two substituents, which may be the same or different. In the latter case, for example, the substituents are selected from alkyl, alkoxy and alkylthio groups which may be substituted by one or more halogen atoms; free and esterified carboxy groups; nitrile and nitro groups; and halogen atoms. Examples of such substituents are methyl, methoxy, nitrile, trifluoromethyl and trifluoromethylthio groups, fluorine and chlorine atoms.

In the above preferred meanings for $R^1$, alkyl groups preferably have up to 4 carbon atoms, cycloalkyl groups preferably have up to 8 carbon atoms, for example, cyclopropyl, cyclobutyl, cyclopentyl and cyclohexyl groups, acyl groups preferably have up to 5 carbon atoms, and aryl groups are for example phenyl groups that are unsubstituted or substituted as defined above for phenyl groups $R^1$.

An esterified carboxyl group —COOR is, for example, an ester formed with an unsubstituted or substituted aliphatic, cycloaliphatic, cycloaliphatic-aliphatic, aryl, araliphatic, heterocyclic or heterocyclic-aliphatic alcohol having up to 20 carbon atoms or is, for example, a silyl or stannyl ester.

R may represent, for example a straight or branched chain substituted or unsubstituted alkyl, alkeyl or alkynyl group having up to 18 carbon atoms, preferably up to 8 carbon atoms, and especially up to 4 carbon atoms, for example, a methyl, ethyl, n-propyl, iso-propyl, n-butyl, sec-butyl, iso-butyl, tert-butyl, n-pentyl, n-hexyl, allyl, or vinyl group.

An aliphatic group R, especially a methyl group, may be substituted by a cycloalkyl, aryl or heterocyclic group, or R may itself represent a cycloalkyl, aryl or heterocyclic group.

A cycloaliphatic group R may have up to 18 carbon atoms and is, for example, a cyclopentyl, cyclohexyl or adamantyl group. An aryl group may have up to 12 carbon atoms and may have two or more fused rings. An aryl group R is, for example, an unsubstituted or substituted phenyl group, and an unsubstituted or substituted aralkyl group is, for example, a benzyl, p-nitrobenzyl or benzhydryl group.

A heterocyclic group may have one or more heteroatoms, selected from oxygen, nitrogen and sulphur, and up to 14 atoms in total. A heterocyclic group is, for example, an oxygen-containing heterocyclic group, for example, a tetrahydropyranyl or phthalidyl group.

A stannyl group R may have up to 24 carbon atoms, for example, R may represent a stannyl group having three substituents, which may be the same or different, selected from alkyl, alkenyl, cycloalkyl, aryl, aralkyl, alkoxy and aralkoxy groups, for example, alkyl groups having up to 4 carbon atoms for example, n-butyl groups, phenyl and benzyl groups, especially three n-butyl groups.

A silyl group R may also have up to 24 carbon atoms and three substituents, which may be the same or different, selected from alkyl, alkenyl, cycloalkyl, aryl and aralkyl groups, for example, alkyl groups having up to 4 carbon atoms, for example, methyl and t-butyl groups.

Any group R that is capable of substitution may be substituted. Examples of substituents are given above in relation to $R^1$. Substituents for phenyl groups are, for example, as described above in relation to preferred groups $R^1$.

The group R may be removable by hydrolysis, by reduction or by enzyme action to give the free acid. A group R that may be removed readily without substantial degradation of the rest of the molecule is particularly useful as a carboxyl protecting group. Examples of esters that are readily split by reduction are arylmethyl esters, for example, benzyl, p-nitrobenzyl, benzhydryl and trityl esters. Reduction of an ester, for example, an arylmethyl ester, may be carried out using hydrogen and a metal catalyst, for example, a noble metal, for example, platinum, palladium or rhodium, which catalyst may be supported, for example, on charcoal or kieselguhr.

A p-nitrobenzyl ester may be split, alternatively, first by reduction of the nitro group, and then by hydrolysis. The nitro group may be reduced, for example, using a metal reducing agent, for example, zinc in acetic acid, aqueous tetrahydrofuran or acetone. The pH should be maintained within the range of from 3 to 6, preferably from 4 to 5.5, preferably by the use of aqueous hydrochloric acid. Other reducing agents are, for example, aluminum amalgam in a moist ether, for example, tetrahydrofuran, and iron and ammonium chloride in an aqueous ether, for example, aqueous tetrahydrofuran. Reduction of the nitro group is followed by hydrolysis which may occur in situ during reduction of the nitro group or which may be carried out subsequently by treatment with an acid.

A stannyl ester, for example, a tri-n-butyl stannyl ester, may be split readily by hydrolysis, for example, or by solvolysis, for example, using water, an alcohol, a phenol or a carboxylic acid, for example, acetic acid.

In some cases it may be preferable if the ester group is removable under physiological conditions, that is to say, the ester group is split off in vivo to give the free acid, for example, an acyloxymethyl ester, e.g. an acetoxymethyl or pivaloyloxymethyl ester, an aminoalkanyloxymethyl ester, for example, an L-glycyloxymethyl, L-valyloxymethyl or L-leucyloxymethyl ester, or a phthalidyl ester, or an optionally substituted 2-aminoethyl ester, for example, a 2-diethylamino-ethyl or 2-(1-morpholino)-ethyl ester.

Preferred esters are the p-nitrobenzyl, phthalidyl and pivoloyloxymethyl esters.

An ester of formula I, or of any other free acid described herein, may be prepared by reaction with an alcohol, phenol or stannanol or a reactive derivative thereof. The reaction is preferably carried out under mild conditions in order to prevent rupture of the ring or ring system, for example, under neutral or mild acidic or basic conditions, and at temperatures within the range from −70° to +35° C.

An alkyl, alkoxyalkyl or aralkyl ester may be prepared by reaction of an acid of formula I or any other free acid with the appropriate diazoalkane or diazoaralkane for example, diazomethane or diphenyldiazomethane. The reaction is preferably carried out in an ether, ester or halogenohydrocarbon as solvent, for example, in diethyl ether, ethyl acetate or dichloromethane. In general, temperatures below room temperature are preferred, for example, from −15° to +15° C.

An ester derived from an alcohol may also be produced by reaction of a reactive derivative of the alcohol, for example, a halide, for example a chloride, bromide or iodide, or a hydrocarbonsulphonyl derivative, for example, a mesyl or tosyl ether, with a salt of an acid of formula I or another free acid described herein for example, an alkali or alkaline earth metal salt, for example, a lithium, sodium, potassium, calcium or barium salt or an amine salt, for example, a triethylammonium salt. This reaction is preferably carried out in a substituted sulphoxide or amide solvent for example, in dimethyl sulphoxide, dimethylformamide or hexamethylphosphoramide or, alternatively, an ester may be prepared by reaction of the acid with the alcohol in the presence of a condensing agent, for example, dicyclohexylcarbodiimide.

A stannyl ester may be formed by reaction of a carboxylic acid of formula I or another free acid described herein, or a salt thereof with a reactive tetravalent tin compound, especially a trialkyl tin oxide.

The present invention also provides the salts of those compounds of the invention that have salt-forming groups, especially the salts of free acids of formula I and the acid addition salts of compounds of formula I having a basic group. The salts are especially physiologically tolerable salts, for example, alkali metal and alkaline earth metal salts, for example, sodium, potassium, lithium, calcium and magnesium salts, ammonium salts and salts with an appropriate organic amine; also physiologically tolerable acid addition salts, where appropriate, with suitable inorganic and organic acids, for example, hydrochloric acid, sulphuric acid, carboxylic and organic sulphonic acids, for example, trifluoroacetic acid and p-toluene-sulphonic acid. Some compounds of formula I which contain a basic center may exist as Zwitterions; such salts are also part of this invention.

A salt of a free acid of formula I may be produced by reacting the free acid with the appropriate base in a solvent, preferably under conditions under which the salt precipitates. In the case of an alkali metal salt, for example, a sodium or potassium salt, the preferred base is an alkoxide.

A salt may be produced directly from an ester by splitting off the ester group under suitable reaction conditions, for example, catalytic reduction of an ester, for example, a p-nitrobenzyl ester, in an aqueous/organic solvent, for example, comprising water and ethyl acetate, dioxane, or tetrahydrofuran, in the presence of an appropriate metal salt, especially a bicarbonate, for example, in an equivalent amount or in a slight excess, yields a salt directly.

The invention also provides a process for the production of a penem derivative of the general formula I, which comprises reacting a compound of the general formula II

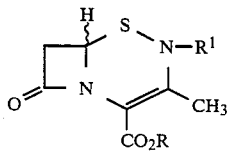

in which R and $R^1$ are as defined above, with a tervalent organophosphorus compound and, if desired, carrying out any one or more of the following steps in any desired order:

(i) converting an ester of formula I into the corresponding free acid,
(ii) converting a free acid of fromula I into an ester thereof,
(iii) transesterifying a compound of formula I,
(iv) converting a free acid or an ester of formula I into a salt, or a salt into the free acid, an ester or another salt.

The tervalent organophosphorus compound is especially one of the general formula $PR^2R^3R^4$ wherein $R^2$, $R^3$ or $R^4$, which may be the same or different, each represents an unsubstituted or substituted hydrocarbon group, for example, a straight or branched chain aliphatic for example alkyl group, an unsubstituted or substituted cycloaliphatic for example cyclopentyl or cyclohexyl group, an unsubstituted or substituted aryl for example, phenyl group; or an unsubstituted or substituted hydrocarbon group in which one or more carbon atoms are replaced by hetero atoms, especially nitrogen, oxygen and sulphur atoms, for example, alkoxy groups, amine groups, and aromatic and nonaromatic heterocyclic groups. Preferred tervalent organophosphorus compounds are triphenylphosphine, tributylphosphine, trimethylphosphite and triethylphosphite.

A further preferred group of tervalent organophosphorus compounds are those in which, in $PR^2R^3R^4$ one or more of the groups $R^2$, $R^3$ and $R^4$ comprises an insoluble polymer, which aids removal after the reaction. Generally one polymeric substituent is adequate.

Another preferred group of tervalent organophosphorus compounds are those in which, in $PR^2R^3R^4$, one or more of the groups $R^2$, $R^3$ and $R^4$ comprise a cationic or anionic center, for example, a quaternary ammonium group or a carboxylate or sulphate group. The presence of a charged group assists removal of the resulting organophosphorus sulphide, for example, by partition or by absorption on an insoluble ion exchange resin or by extraction into an aqueous solution at an appropriate pH, when the organophosphorus sulphide is water soluble.

The reaction of the compound of formula II with the tervalent organophosphorus compound is preferably carried out in a dry, inert organic solvent or diluent, for example, an oxygenated hydrocarbon other than an alcohol, for example, an ether or an ester, for example, diethylether, tetrahydrofuran or ethyl acetate; an aromatic hydrocarbon for example, benzene or toluene; a halogenated hydrocarbon, for example, methylene chloride or chloroform; or another organic solvent, for example, dimethylformamide or acetonitrile. The preferred solvents are acetonitrile and ethyl acetate. A mixture of two or more solvents or diluents may be used. The reaction may be carried out at a temperature from 0° to 80° C., preferably from 0° to 20° C., and it is preferable to use at least 1 equivalent of the phosphorus compound per equivalent of the compound of formula II.

The resulting compound of formula I may be isolated from the reaction mixture, for example, by chromatography or crystallisation. The compound of formula I may be obtained as a mixture of the 5R- and 5S-isomers. These isomers can be isolated, if desired, or the compound of formula I can be used in the form of the isomeric mixture.

If R in formula I represents an esterifying group, this may be removed in the usual manner, depending on the nature of the ester group, for example, by hydrolysis, reduction, or enzymatically, to yield the free acid. A free acid or an ester may be converted into a salt, especially a physiologically tolerable salt, or a salt may be converted into another salt or the free acid or an ester. An ester may be transesterified, or a free acid converted into an ester, for example, to give an ester capable of removal under physiological conditions. Examples of such procedures are given above.

A compound of the general formula II may be produced in various ways, for example, as shown in the reaction scheme below:

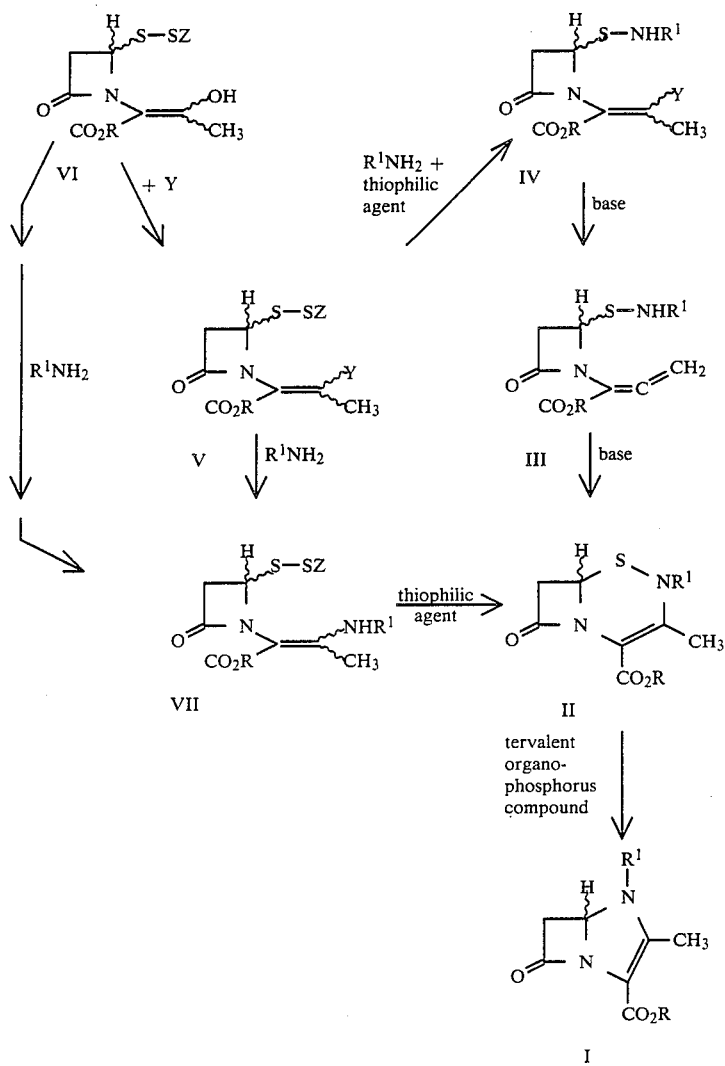

in which

~~~denotes that a group may be cis- or trans- to the group —COOR,

R and $R^1$ are as defined above,

Z represents an unsubstituted or substituted aromatic heterocyclic radical with up to 15, preferably up to 9, carbon atoms and at least one ring nitrogen atom and optionally a further ring heteroatom, which radical is bonded to the dithio group by one of its ring carbon atoms, which is bonded to a ring nitrogen atom by a double bond, or Z represents an acyl radical derived from an organic carboxylic or thiocarboxylic acid, and Y represents a group that is capable of being replaced by a nucleophilic group and is, for example, a sulphonyloxy or phosphinyloxy group or a halogen atom, for example, a radical of the formula

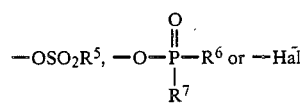

in which $R^5$ represents an aliphatic, cycloaliphatic, aryl or araliphatic group having up to 20 carbon atoms, which may be substituted or unsubstituted, for example, as described above for $R^1$. An aliphatic group $R^5$ is, for example, an alkyl group having up to 8 carbon atoms which may be substituted by one or more halogen atoms, for example, chlorine and bromine atoms. An aryl group $R^5$ has, for example, up to 15 carbon atoms, and may be substituted by one or more substituents, which may be the same or different, selected from alkyl and alkoxy groups, for example, methyl and methoxy groups, and halogen atoms, especially bromine atoms. $R^5$ preferably represents an unsubstituted or substituted aryl group having up to 15 carbon atoms, for example, a phenyl, p-tolyl, p-bromophenyl or p-nitrophenyl group, or an unsubstituted or substituted alkyl group, especially with 1 to 4 carbon atoms, and preferably a methyl or trifluoromethyl group.

In the radical

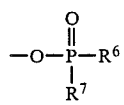

$R^6$ and $R^7$, which may be the same or different, each represents an unsubstituted or substituted alkyl, aryl or aralkyl group, or $R^6$ and $R^7$ together with the phosphorus atom may form a 5- or 6-membered ring, or either or both of $R^6$ and $R^7$ may represent a group $-OR_a^6$ or $-OR_a^7$ respectively, in which $R_a^6$ and $R_a^7$ are as defined above for $R^6$ and $R^7$ respectively and, in the case when $R^6$ represents $-OR_a^6$ and $R^7$ represents $-OR_a^7$, $R_a^6$ and $R_a^7$ may together represent a 5- or 6-membered ring.

A preferred phosphinyloxy group Y is a dimethylphosphinyloxy group.

—Hal represents, for example, a chlorine, bromine or iodine radical.

An aromatic heterocyclic radical Z may be monocyclic or bicyclic and may be substituted, for example, by a lower alkyl group, for example, a methyl or ethyl group, a lower alkoxy group, for example, a methoxy or ethoxy group, a halogen atom, for example, a fluorine or chlorine atom, or an aryl group, for example, a phenyl group.

A heterocyclic radical Z is, for example, a monocyclic five-membered thiadiazacyclic, thiatriazacyclic, oxadiazacyclic or oxatriazacyclic radical of aromatic character, especially a monocyclic five-membered diazacyclic, oxacyclic or thiazacyclic radical of aromatic character, and above all, the corresponding benzdiazacyclic, benzoxocyclic or benzthiazacyclic radicals, wherein the heterocyclic part is five-membered and is of aromatic character.

In radicals Z a substitutable ring nitrogen atom can be substituted, for example, by a lower alkyl group. Examples of such groups Z are 1-methyl-imidazol-2-yl, 1,3-thiazol-2-yl, 1,3,4-thiadiazol-2-yl, 1,3,4,5-thiatriazol-2-yl, 1,3-oxazol-2-yl, 1,3,4-oxadiazol-2-yl, 1,3,4,5-oxatriazol-2-yl, 2-quinolyl, 1-methyl-benzimidazol-2-yl, benzoxazol-2-yl and especially benzthioazol-2-yl groups. Z may also represent an acyl radical of an organic carboxylic or thiocarboxylic acid, for example, an unsubstituted or substituted aliphatic, cycloaliphatic, araliphatic or aromatic acyl or thioacyl group having up to 18, preferably up to 10, carbon atoms, for example, lower alkanoyl groups, for example acetyl and propionyl groups, lower thioalkanoyl groups, for example thioacetyl and thiopropionyl groups, cycloalkanecarbonyl groups, for example a cyclohexanecarbonyl group, cycloalkanethiocarbonyl groups, for example, a cyclohexanethiocarbonyl group, benzoyl, thiobenzoyl, naphthylcarbonyl, and naphthylthiocarbonyl groups, heterocyclic carbonyl and thiocarbonyl groups, for example, 2-, 3- or 4-pyridylcarbonyl, 2- or 3-thenoyl, 2- or 3-furoyl, 2-, 3-, or 4-pyridyl-thiocarbonyl, 2- or 3-thiothenoyl, and 2- or 3-thiofuroyl groups, and corresponding substituted acyl and thioacyl groups, for example acyl and thioacyl groups monosubstituted or polysubstituted by lower alkyl groups, for example, methyl groups, halogen atoms, for example, fluorine and chlorine atoms, lower alkoxy groups, for example, methoxy groups, aryl groups for example phenyl groups, and aryloxy groups, for example phenyloxy groups.

Z preferably represents a

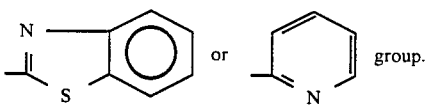

As shown above, a compound of formula II may be produced from a compound VI via compounds V, IV and III, via compounds V and VII, or via compound VII.

Taking the first of these routes, a compound of formula VI may be converted into a compound of formula V by reaction with a compound capable of introducing the group Y at the hydroxyl group of the enol.

Y is a group that can be replaced by a nucleophilic group, especially one that can be replaced readily by a nucleophilic group, for example, a compound capable of yielding a sulphonyloxy or phosphinyloxy group or a halogen atom. Examples of compounds capable of introducing the group Y are the following:

| | |
|---|---|
| $R^5SO_2X$ | VIIIa |
| $R^5SO_2OSO_2R^5$ | VIIIb |
|  | VIIIc |
|  | VIIId |
| $SOX_2$ | VIIIe |
| $PX_3$ | VIIIf |
| $PX_5$ | VIIIg | in which $R^5$, $R^6$ and $R^7$ are defined as above and X represents a fluorine, chlorine or bromine atom, especially a fluorine or chlorine atom.

The reaction is generally carried out in the presence of an inert non-nucleophilic base to neutralise any acid formed.

The base may be organic, for example, a primary, secondary or tertiary amine, for example, a trialkyl amine, for example, triethylamine, dabco [diazabicyclo-(2,2,2)-octane] or N-methyldiisopropylamine, an N,N-dialkylarylamine, for example, N,N-dialkylaniline, or a pyridine which may be unsubstituted or substituted for example, by one or more alkyl groups, for example,

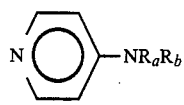

in which $R_a$ and $R_b$ represent the same or different alkyl groups, or lutidine or collidine; or the base may be inorganic, for example, an alkali metal carbonate, bicarbonate or hydroxide, for example, $NaHCO_3$, $Na_2CO_3$ or $NaOH$.

The reaction is preferably carried out in an inert solvent or diluent, for example, as described above, and the reaction temperature may be within the range from −20° to +60° C., preferably from −20° to 0° C.

The resulting compound of formula V may then be converted to a compound of formula IV or of formula VII.

A compound of formula V may be converted to a compound of formula IV by reaction with an amine of the formula $R^1NH_2$, in which $R^1$ is as defined above, in the presence of a thiophilic agent.

The thiophilic agent is especially a thiophilic metal salt, for example, a salt of an element of Group Ib, IIb or VIII of the Periodic Table of the Elements (cf. Advanced Inorganic Chemistry, F. A. Cotton and G. Wilkinson, Interscience), for example, a silver, copper, zinc, nickel, iron, cadmium, mercury or cobalt thiophilic salt, silver and copper salts being preferred. Examples of preferred thiophilic salts are (i) $AgNO_3$, $AgOSO_2CF_3$, $AgOSO_2Me$, $AgBF_4^\ominus$, $AgPF_6^\ominus$, $CuCl$, $CuBr$, $CuCl_2$, $CuBr_2$, $CuOSO_2Me$, $CuOSO_2CF_3$, $CuSO_4$, $Cu(NO_3)_2$ and the corresponding nickel, zinc, iron and cobalt salts; and (ii) $AgOCOCH_3$, $Ag_2CO_3$, $AgO$, $Cu(acac)_2$, $Cu(CO_3)_2$, $Cu_2CO_3$, and $CuOR^7$ in which $R^7$ represents an alkyl group or cycloalkyl group for example, comprising up to 8 carbon atoms, preferably $CH_3$, $C_2H_5$, or t-butyl. Silver acetate is particularly preferred.

Because a proton is liberated in the course of the reaction with the thiophilic agent, it is desirable that the proton be removed by a base so the reaction can go to completion. The base preferably has a $pK \geq 4$, so if the metal salt is itself sufficiently basic, for example, the salts of group (ii) above, it is not necessary to incorporate a further base in the reaction mixture. If, however, the metal salt is only weakly basic, for example, the salts of group (i) above, then it is preferable to use a further base, having a $pK \geq 4$. The term "thiophilic agent" is used herein to mean a thiophilic metal salt alone, or a thiophilic metal salt plus base, as appropriate.

The base may be inorganic or organic, and preferred organic bases are pyridine, lower alkyl substituted pyridines, alkylamine substituted pyridines, and lower alkyl substituted piperidinese.g. 2,2,6,6-tetramethylpiperidine, and trisubstituted amines, for example, trialkylamines, for example triethylamine and ethyldiisopropylamine, and N-alkyl-arylamines, for example, 1,8-bis-(dimethylamino)naphthalene, or N,N-dimethylphenylamine. Examples of preferred inorganic bases are metal hydrides, e.g. sodium hydride, and metal carbonates, for example, sodium carbonate.

The reaction is preferably carried out in an inert solvent or diluent, which is preferably highly purified. Any solvent or diluent may be used provided it is not hydroxylic. Examples of solvents and diluents are given above in relation to the conversion of compound II to compound I, chlorinated hydrocarbons, for example, methylene chloride and chloroform, being preferred. The reaction temperature is, for example, within the range from −20° to +60° C., preferably from 0° to 20° C.

The amine is preferably used in an amount equivalent to the amount of compound V and is preferably added to a stirred solution of the compound V and the thiophilic agent.

The group Y may be removed from a compound of formula IV by treatment with a base to give an allene III as a transient intermediate which then cyclises, in the presence of the base, to give a compound of formula II. The base should have a pKa sufficient to cause the elimination of the group Y at a suitable rate, for example, the pKa is preferably greater than 7 when Y represents a mesylate group. Examples of bases are tertiary amines, for example, triethylamine and preferably dabco.

An inert non-protic solvent or diluent is preferably used, especially chloroform or toluene, and the reaction temperature is, for example, from −20° to +100° C., preferably from 20° to 40° C.

As indicated above, compound V may be converted into compound VII in another route for the production of compound II: A compound of formula V is reacted with a primary amine of the formula $R^1NH_2$ in which $R^1$ is as defined above. No thiophilic agent need be present in this case as the amine replaces the group Y rather than the group —SZ as in the previous case.

The amine and compound V may be used in equimolar amounts. It is generally preferable, however, to carry out the reaction in the presence of a base to neutralise any acid liberated, so excess amine for example two equivalents or more may be used. Alternatively, another base may be provided in addition to the amine.

The base may be organic, for example, a primary, secondary or tertiary amine, for example, a trialkylamine, for example, triethylamine, dabco, [diazabicyclo(2,2,2)octane] or N-methyldiisopropylamine, an N,N-dialkylamine, for example, N,N-dialkylanaline, or

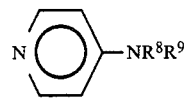

in which $R^8$ and $R^9$ represent the same or different alkyl groups; or the base may be inorganic, for example, an alkali metal carbonate or bicarbonate or hydroxide, for example $NaHCO_3$, $Na_2CO_3$, or $NaOH$.

If the pK of the amine $R^1NH_2$ is equal to or less than 7, the reaction tends to be slow, so it is preferable to carry out the reaction in the presence of a base that is inert to the reaction and which has a pK greater than 7 to accelerate the reaction. It will be appreciated that one base may act as both catalyst and acid acceptor.

The reaction is preferably carried out in a dry, inert solvent, for example, as described above in relation to the conversion of compound II to compound I, especially in methylene chloride. The reaction temperature is, for example, from −20° to 60° C., preferably from −20° to +20° C.

The resulting compound of formula VII is generally produced as a mixture of E and Z isomers. Either the E- or Z-isomer or a mixture of E and Z-isomers may then be converted to a compound of formula II by treatment with a thiophilic agent, preferably in an inert solvent or diluent. (It will be appreciated that the E-isomer must be converted to the Z-isomer before cyclisation can occur. This isomerisation occurs in situ under the reaction conditions for the conversion of compound VII to compound II.)

Thiophilic agents are as described above for the conversion of compound V to compound IV, and may be used in equimolar amounts or in an excess, preferably a molar excess, over compound VII. The reaction temperature is, for example, from 0° to 100° C., preferably from 60° to 80° C., and it will be appreciated that the thiophilic agent must be chosen with the proposed reaction temperature in mind, so there is not substantial decomposition of the thiophilic agent during the reaction. Silver acetate is the preferred thiophilic agent.

Solvents and diluents are also as described above for the conversion of compound V to IV; benzene is the preferred solvent or diluent. Vigorous stirring is required if the thiophilic agent is partially insoluble in the reaction mixture.

Yields are improved by using the reactants in dilute solution, and the preferred concentration range for the thiophilic agent and for compound VII is from 0.1 g to 1 g in 1000 ml. It is also preferable to use a highly purified and dried solvent, and a finely divided thiophilic agent.

The reaction is preferably carried out by refluxing a mixture of 1 g of compound VII in 1 liter of dry benzene containing finely ground silver acetate. The mixture is preferably refluxed under an inert gas, for example, argon or nitrogen, with vigorous stirring.

A compound of formula VII may be produced directly from a compound of formula VI by treatment with a salt of an amine of the formula $R^1NH_2$, in which $R^1$ is as defined above, for example, an acid addition salt, especially a hydrogen halide addition salt, for example, the hydrochloride addition salt. The reaction is generally carried out in the presence of a tertiary amine, for example pyridine, in a solvent or diluent, for example, an alcohol, for example, ethanol or methanol. The reaction temperature is, for example, from 20° to 100° C., preferably from 40° to 60° C.

A compound of formula VI which has the R-configuration at position 4 may be produced from 6-amino penicillanic acid, a relatively inexpensive and readily available product, for example, as shown below:

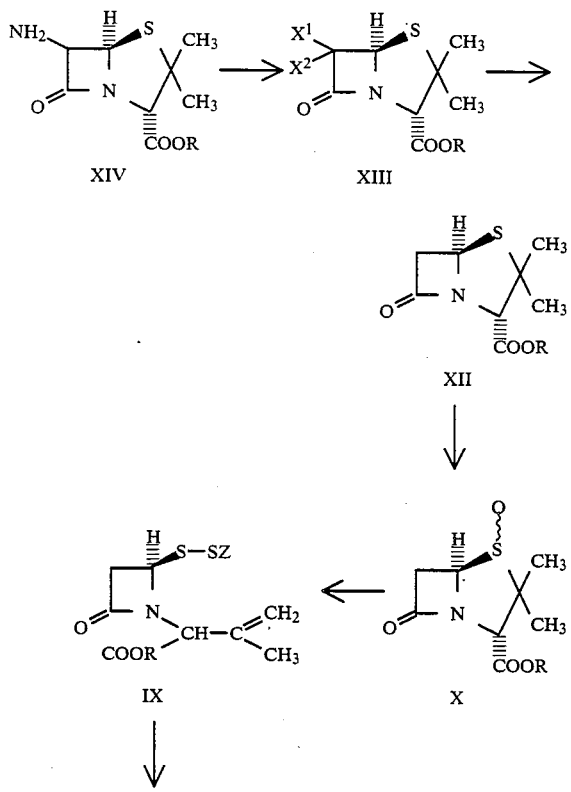

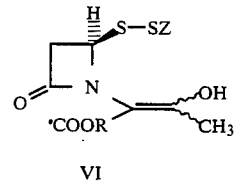

In the above scheme R is as defined above and $X^1$ and $X^2$ both represent halogen atoms, or one represents a halogen atom and the other a hydrogen atom. A halogen atom is preferably a bromine or iodine atom. ⁓⁓ is also as defined above.

A compound of formula VI may be produced by converting a compound of formula IX

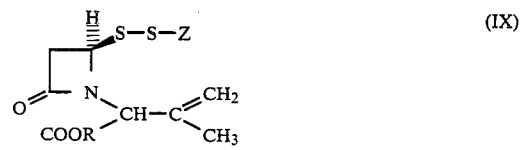

in which R and Z are as defined above, into the corresponding enol.

This is preferably carried out by ozonolysis, generally via an intermediate ozonide of the general formula

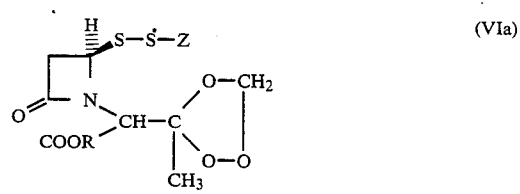

Ozone is usually employed in the presence of a solvent, for example, an alcohol, for example a lower alkanol, for example methanol or ethanol, a ketone, for example a lower alkanone, for example acetone, an optionally halogenated aliphatic, cycloaliphatic or aromatic hydrocarbon, for example a halogeno-lower alkane, for example methylene chloride or carbon tetrachloride, an ester, for example methyl acetate or ethyl acetate, or a mixture of two or more solvents, including an aqueous mixture, and with cooling or slight warming, for example at temperatures from −90° C. to +40° C., preferably from −60° C. to +0°.

An ozonide intermediate VIa can be split by reduction to give a compound of the formula VI for which it is possible to use catalytically activated hydrogen, for example hydrogen in the presence of a heavy metal hydrogenation catalyst, for example a nickel catalyst, or a palladium catalyst, preferably on a suitable carrier, for example, calcium carbonate or charcoal; or a chemical reducing agent, for example, a reducing heavy metal, including a heavy metal alloy or amalgam, for example zinc, in the presence of a hydrogen donor, for example, an acid, for example acetic acid, or an alcohol, for example a lower alkanol, a reducing inorganic salt, for example an alkali metal iodide, for example sodium iodide, in the presence of a hydrogen donor, for example, an acid, for example acetic acid, a reducing sulphide compound for example, sulphur dioxide or a di-lower alkyl sulphide, for example dimethyl sulphide, a reducing organic phosphorus compound, for example a phosphine, which can optionally contain substituted aliphatic or aromatic hydrocarbon radicals as substituents, for example tri-lower alkylphosphines, for example tri-n-butylphosphine, or triarylphosphines, for example triphenylphosphine, also phosphites which contain optionally substituted aliphatic hydrocarbon radicals as substituents, for example tri-lower alkyl phosphites, usually in the form of the corresponding alcohol adduct compounds, for example trimethylphosphite, or phosphorus acid triamides which contain optionally substituted aliphatic hydrocarbon radicals as substituents, for example hexa-lower alkyl phosphorus acid triamides, for example hexamethyl-phosphorus acid triamide, the latter preferably in the form of a methanol adduct, or tetracyanoethylene. The splitting of the ozonide, which is usually not isolated, is normally carried out under the conditions which are employed for its manufacture, that is to say in the presence of a suitable solvent or solvent mixture, and with cooling or slight warming.

The ozonolysis is preferably carried out in ethyl acetate or dichloromethane which comprises from 0 to 50% by volume of methanol. A mixture of 75% dichloromethane and 25% methanol is particularly preferred. The preferred reducing agents are dimethyl sulphide and sulphur dioxide.

The ozonolysis may result, inter alia, in a mixture of isomers VIb and VIc about the double bond i.e.

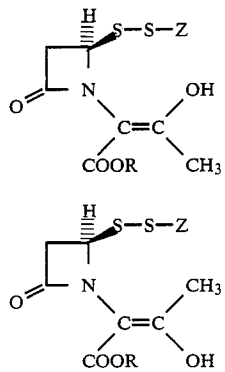

These isomers are readily interconvertible, and compounds of the formulae VIb and VIc can also exist in the tautomeric keto form.

A compound of formula IX is preferably produced by reacting a compound of formula

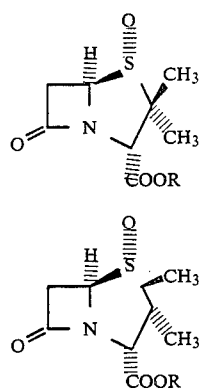

in which R is as defined above with a compound of formula

H—S—Z  (XI)

in which Z is as defined above.

This reaction may be carried out by merely heating the compound of formula X with the compound of formula XI preferably in a nitrogen or argon atmosphere, in an inert solvent or diluent at a temperature from 50° to 150° especially from 80° to 120°. Suitable solvents are those which possess a sufficiently elevated boiling point to achieve the necessary reaction temperature and in which the starting materials and product are stable at the temperature of the reaction. Examples of solvents are benzene, toluene, ethylacetate, acetonitrile, dioxane, N,N-dimethyl formamide and N,N-dimethylacetamide.

The compound of formula X is preferably produced from a compound of formula XII

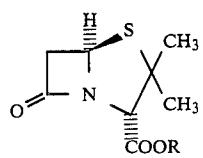

in which R is defined as above, by means of oxidation.

The oxidation may be carried out by any method suitable for oxidizing sulphides to the corresponding sulphoxides. Oxidising agents are, for example, hydrogen peroxide, periodates e.g. sodium periodate, ozone, peracids e.g. peracetic acid, perbenzoic acid, substituted perbenzoic acids e.g. m-chloroperbenzoic acid, and permanganate salts, e.g. potassium permanganate. Preferred oxidizing agents are hydrogen peroxide and m-chloroperbenzoic acid.

The oxidation is preferably conducted in an inert solvent at a preferred temperature from −20° to +30°. Preferred solvents are ethyl acetate, methylene chloride, chloroform, acetonitrile, and lower alcohols, for example methanol and ethanol.

A compound of formula XII may be prepared by catalytically hydrogenating a compound of the general formula XIII

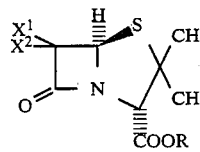

in which $X^1$ and $X^2$ are the same and each represents a halogen atom, or $X^1$ represents a hydrogen atom and $X^2$ represents a halogen atom, and R represents a hydrogen atom or a carboxyl esterifying group.

An example of such a process in which R represents a hydrogen atom is given in J. Chem. Soc. 2623 (1969).

Some compounds of formula XIII are known and can be prepared according to known procedures. One such procedure which is described in J. Chem. Soc., 2623 (1969), involves the treatment of 6-amino penicillanic acid simultaneously with nitrous acid and a halogenating agent. The use of sodium bromide as the halogenating agent results in a compound of formula XIII in which X represents a hydrogen atom, Y represents a bromine atom and R represents a free carboxyl group, with sodium iodide giving the corresponding compound in which Y represents an iodine atom, and bromine giving the dibromo analogue.

A compound of formula XIII in which R represents —CH₂Ph, X represents a hydrogen atom and Y represents an iodine atom, and the dibromo analogue thereof, may both be prepared by the process described in J. Org. Chem., 43, 2960 (1977).

Other compounds of formula XIII may be prepared analogously.

6-Aminopenicillanic is an advantageous starting material as it is readily available and relatively inexpensive. It will be appreciated that the use of a compound analogous to 6-aminopenicillanic acid but having a different stereochemical configuration will result in the production of a compound of formula VI having the corresponding stereochemical configuration.

It is advisable to esterify a free carboxyl group in a compound of formula III or VII prior to cyclization. Although an ester group may be introduced immediately prior to cyclization, it is preferable to esterify the carboxyl group at an earlier stage in the preferred reaction sequence, for example, to esterify a free carboxyl group in a compound of formula XII, XII, XIV or X to ensure that the carboxyl group does not take part in any of the subsequent reactions.

At each stage of the preferred reaction sequence, the desired compound may be isolated from the reaction mixture and, if desired, purified by appropriate techniques generally used for the purification of organic compounds, for example, chromatography or crystallization.

As indicated above, various intermediates may be produced in the form of mixture of isomers of various kinds. Such a mixture may be separated or resolved at any stage, or the isomeric mixture may be used per se for subsequent reactions.

All of the compounds that are provided by the invention may exist in any appropriate isomeric form, as discussed above, either as a pure isomer or as a mixture of any two or more isomers.

The compounds of formula I and salts thereof are β-lactamase inhibitors, and the compounds are generally stable to the action of β-lactamases produced by gram-positive organisms, for example, by *Staphylococcus aureus* and gram negative organisms, for example, Enterobactercloacae. They also possess antibacterial properties themselves and may be used, for example, to treat bacterial infections in human and other animals.

The invention accordingly provides a compound of formula I or a physiologically tolerable salt thereof, or a mixture of two or more such substances as active ingredient, in admixture or conjunction with a pharmaceutically suitable carrier. The preparation may also comprise one or more other pharmaceutically active substances, for example, another antibacterial substance, especially one which has a β-lactam ring. The preparations may be in a form suitable for enteral or parenteral administration, for example, for oral, intravenous, or intramuscular administration, for example, as tablets, capsules, syrups, or sterile injectable or infusible solutions. The preparations are advantageously in unit dosage form and preferably comprise from 10 to 2000 mg of the active ingredient. The daily dosage of the active substance is generally from 20 to 8000 mg, in divided doses, generally up to 4 doses.

The invention also provides the use of a compound of the invention as a β-lactamase inhibitor and/or as an antibacterial agent.

The invention further provides a pharmaceutical preparation which comprises a compound of the general formula I or a physiologically tolerable salt thereof, or a mixture of two or more such substances, in unit dosage form.

The invention also provides a pharmaceutical preparation which comprises a compound of the general formula I or a physiologically tolerable salt thereof or a mixture of two or more such substances, and one or more further pharmaceutically active substances, for example, as described above and, for example, in unit dosage form.

Unit dosages are preferably as described above.

The following Table gives examples of compounds of the general formula I:

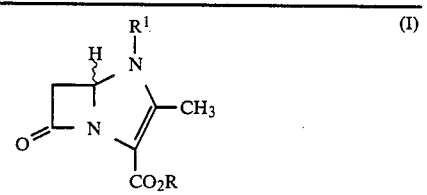

(I)

| | $R^1$ | R |
|---|---|---|
| 1. | phenyl | H |
| 2. | o-cyanophenyl | H |
| 3. | m-cyanophenyl | H |
| 4. | p-cyanophenyl | H |
| 5. | o-trifluoromethylphenyl | H |
| 6. | m-trifluoromethylphenyl | H |
| 7. | p-trifluoromethylphenyl | H |
| 8. | o-nitrophenyl | H |
| 9. | m-nitrophenyl | H |
| 10. | p-nitrophenyl | H |
| 11. | o-fluorophenyl | H |
| 12. | m-fluorophenyl | H |
| 13. | p-fluorophenyl | H |
| 14. | 2,3-difluorophenyl | H |
| 15. | 2,4-difluorophenyl | H |
| 16. | 2,5-difluorophenyl | H |
| 17. | 2,6-difluorophenyl | H |
| 18. | 3,5-difluorophenyl | H |
| 19. | 3,4-difluorophenyl | H |
| 20. | methyl | H |
| 21. | ethyl | H |
| 22. | —CH₂CF₃ | H |
| 23. | —CH₂CN | H |
| 24. | benzyl | H |
| 25. | —CH₂CO₂H | H |
| 26. | —CH₂CO₂CH₃ | H |
| 27. | —CH₂CO₂C₂H₅ | H |
| 28. | —CH₂CO₂—n-C₃H₇ | H |
| 29. | —CH₂CO₂—iso-C₃H₇ | H |
| 30. | —CH₂CO₂—n-C₄H₉ | H |
| 31. | —CH₂CO₂—sec-C₄H₉ | H |
| 32. | —CH₂CO₂—iso-C₄H₉ | H |
| 33. | —CH₂CO₂—tert-C₄H₉ | H |
| 34. | —CH₂CO₂CH=CH₂ | H |
| 35. | —CH₂CONH₂ | H |
| 36. | —CH₂CONHCH₃ | H |
| 37. | —CH₂CONHC₂H₅ | H |
| 38. | —CH₂CONH—n-C₃H₇ | H |
| 39. | —CH₂CONH—iso-C₃H₇ | H |
| 40. | —CH₂CONH—n-C₄H₉ | H |

-continued (I)

[structure of compound I with R¹, N-H, CH3, CO2R, azetidinone ring]

| | R¹ | R |
|---|---|---|
| 41. | —CH₂CONH—iso-C₄H₉ | H |
| 42. | —CH₂CONH—sec-C₄H₉ | H |
| 43. | —CH₂CONH—tert-C₄H₉ | H |
| 44. | —CH₂CON(CH₃)₂ | H |
| 45. | —CH₂CON(C₂H₅)₂ | H |
| 46. | —CH₂CON(n-C₃H₇)₂ | H |
| 47. | —CH₂CON(iso-C₃H₇)₂ | H |
| 48. | —CH₂CON(n-C₄H₉)₂ | H |
| 49. | —CH₂CON(iso-C₄H₉)₂ | H |
| 50. | —CH₂CON(sec-C₄H₉)₂ | H |
| 51. | —CH₂CON(tert-C₄H₉)₂ | H |
| 52. | —CH₂CON(azetidine) | H |
| 53. | —CH₂CON(pyrrolidine) | H |
| 54. | —CH₂CON(piperidine) | H |
| 55. | —CH₂CON(azepane) | H |
| 56. | —CH₂CONHC₆H₅ | H |
| 57 to 112 | as compounds 1 to 56 respectively | p-nitrobenzyl |
| 113 to 168 | as compounds 1 to 56 respectively | phthalidyl |

Compounds 1 to 56 may be in the form of a salt, especially a physiologically tolerable salt.

Compounds of the general formulae II, III, IV and VIII are also part of this invention.

The following Examples illustrate the invention. In them, temperatures are expressed in degrees Celsius and ratios of solvents for chromatography are by volume.

EXAMPLE 1

(a)

4'-Nitrobenzyl-2-[4R-(2-benzthiazolyldithio)-2-oxo-1-azetidinyl]-3-ethylamino crotonate (VII)

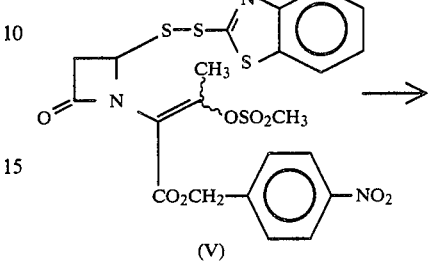

(V)

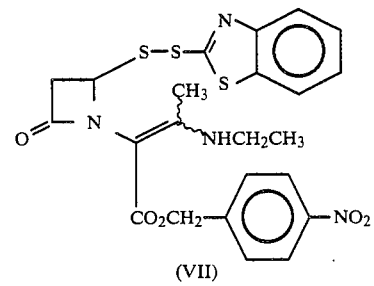

(VII)

A solution of 5.0 g of 4'-nitrobenzyl-2-[4R-(2-benzthiazolyldithio)-2-oxo-1-azetidinyl]-3-methylsulphonyloxy crotonate in 105 ml dry dichloromethane was cooled to $-20°$ under an argon atmosphere, and to this was added 1.23 ml ethylamine. After stirring for one hour, the solution was filtered through "Hyflo" (Trade Mark), evaporated in vacuo and chromatographed on silica gel eluting with hexane/ethyl acetate (1:1). 4.04 g of 4'-nitrobenzyl-2-[4R-(2-benzthiazolyldithio)-2-oxo-1-azetidinyl]-3-ethylamino crotonate (88% of the theoretical yield), were obtained as a pale yellow solid.

mp 149.5°–150.5° $\nu_{max}$ (film) 1770, 1660 cm$^{-1}$.

$\delta$ ppm (CDCl₃) 1.23 (3H, t, J=7.5 Hz, CH₂$\underline{CH_3}$), 2.11 (3H, S, CH₃) 2.90–3.73 (4H, M, $\underline{CH_2}$CH₃, H-3) 5.22 (3H, m, $\underline{CH_2}$Ph, H-4) 7.20–8.38 (8H, m, aromatics) 9.10 (1H, m, $\underline{NH}$).

(b)

2-Ethyl-4-(4-nitrobenzyloxycarbonyl)-1-thia-2-azacephem (II)

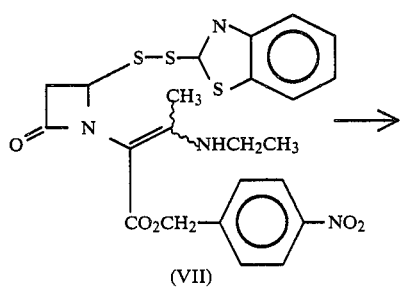

(VII)

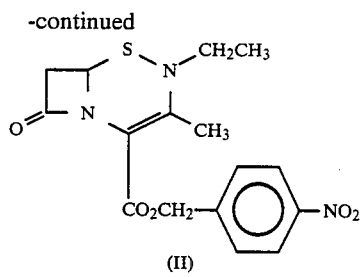

To a solution of 4.7 g of 4'-nitrobenzyl-2-[4R-(2-benzthiazolyldithio)-2-oxo-1-azetidinyl]-3-ethylamino crotonate in 3000 ml dry benzene under an argon atmosphere, was added 5 g of finely divided silver acetate. The vigorously stirred solution was refluxed until the reaction was shown by thin layer chromatography to be essentially complete. The suspension was filtered through "Hyflo" then evaporated in vacuo, and the residue was chromatographed on silica gel eluting with hexane/ethyl acetate (1:1) 1.46 g of 2-ethyl-4-(4-nitrobenzyloxycarbonyl)-6R-1-thia-2-azacephem (50.6% of the theoretical yield) was obtained as a white crystalline solid.

mp. 110°–112°.$\nu_{max}$(CHCl$_3$) 1775, 1706 cm$^{-1}$

δ ppm (CDCl$_3$) 1.77 (3H, t, J=7 Hz, CH$_2$CH$_3$), 2.43 (3H, S, CH$_3$) 2.77 (1H, dd, Jab=15.5 Hz, Jax=2 Hz, H-7), 3.13–3.87 (2H, m, CH$_2$CH$_3$) 3.80 (1H, dd, Jab=15.5 Hz, Jbx=5 Hz, H-7) 4.38 (1H, dd, Jax=2 Hz, Jbx=5 Hz, H-6) 5.35 (2H, S, CH$_2$Ph) 7.43–8.47 (4H, m, aromatics).

m/e found 363.0837; C$_{16}$H$_{17}$N$_3$O$_5$S requires 363.0888.

(c) 1-Ethyl-3-(4-nitrobenzyloxycarbonyl)-azapenem

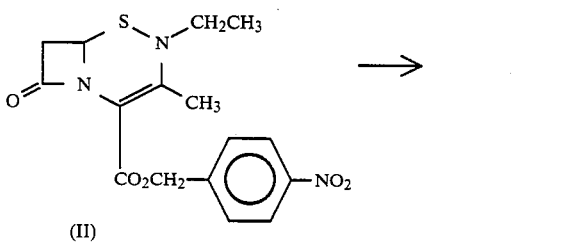

A solution of 1.209 g of 2-ethyl-4-(4-nitrobenzyloxycarbonyl)-6R-1-thia-2-azacephem in 20 ml dry acetonitrile was added rapidly to a vigorously stirred solution of 0.95 g of triphenylphosphine in 20 ml acetonitrile. After 5 minutes the pale yellow solution was evaporated in vacuo, and chromatography was carried out on silica gel, eluting first with hexane/dichloromethane (1:1) and then hexane with ethyl acetate (1:1).

0.556 g of 1-ethyl-3-(4-nitrobenzyloxycarbonyl)-5ξ-azapenem (50.4% of the theoretical yield) was obtained as a yellow crystalline solid.

mp. 116°–117°.$\nu_{max}$(CHCl$_3$) 1790, 1680 cm$^{-1}$.

δ ppm (CDCl$_3$) 1.23 (3H, t, J=7 Hz, CH$_2$CH$_3$), 2.29 (3H, S, CH$_3$), 3.20 (1H, dd, Jab=16 Hz, Jax=1 Hz, H-6), 3.77 (1H, dd, Jab=16 Hz Jbx=2.5 Hz, H-6) 2.88–3.53 (2H, m, CH$_2$CH$_3$), 5.13 (1H, d, Jab=14 Hz, CH$_2$Ph) 5.22 (1H, dd, Jax=1 Hz, Jbx=2.5 Hz, H-5) 5.48 (1H, d, Jab=14 Hz, CH$_2$Ph) 7.33–8.37 (4H, m, aromatics).

m/e Found 331.1184°, C$_{16}$H$_{17}$N$_3$O$_5$ requires 331.1168.

EXAMPLE 2

(a) 4-Nitrobenzyl-2-[4R-(2-benzthiazolyldithio)-2-oxo-1-azetidinyl]-3-anilino crotonate (VII)

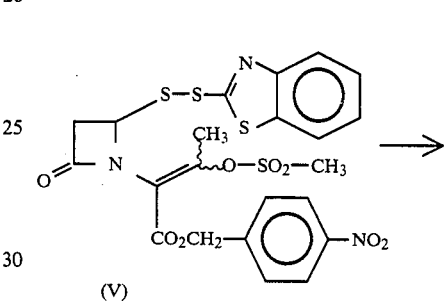

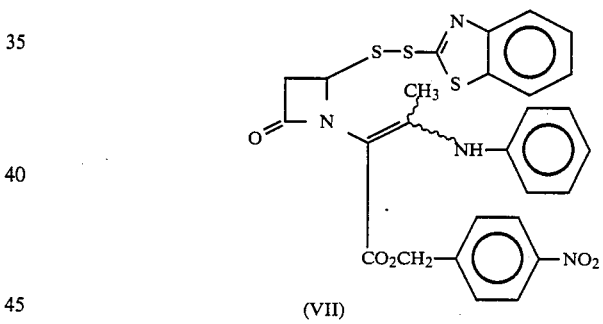

To a stirred solution of 2.274 g of 4'-nitrobenzyl-2-[4R-(2-benzthiazolyldithio)-2-oxo-1-azetidinyl]-3-methylsulphonyloxy crotonate in 60 ml dry dichloromethane was added 0.7 ml of purified aniline followed by a solution of 0.438 g of diazabicyclo[2,2,2]-octane in 6 ml dry dichloromethane. After having been stirred for one hour the solution was evaporated in vacuo and chromatographed on silica gel eluting with hexane/ethyl acetate (1:1), 1.59 g (70% of the theoretical yield) of 4'-nitrobenzyl-2-[4R-(2-benzthiazolyldithio)-2-oxo-1-azetidinyl]-3-anilino crotonate were obtained.

$\nu_{max}$ (film) 1765, 1664 cm$^{-1}$.

δ ppm (CDCl$_3$) 2.13 (3H, S, CH$_3$) 3.10 (1H, dd, Jab=16 Hz, Jax=2.5 Hz, H-3) 3.49 (1H, dd, Jab=16 Hz, Jbx=4.5 Hz, H-3) 5.27 (3H, m, H-4, PhCH$_2$) 6.86–8.33 (13H, m, aromatics) 10.80 (1H, S, NH).

(b)
2-Phenyl-4-(4-nitrobenzyloxycarbonyl)-1-thia-2-azacephem (II)

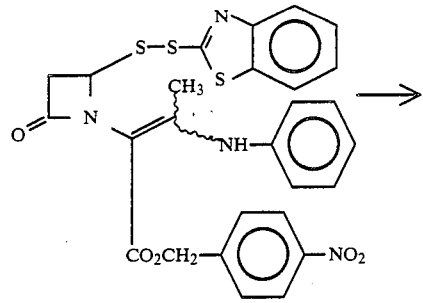

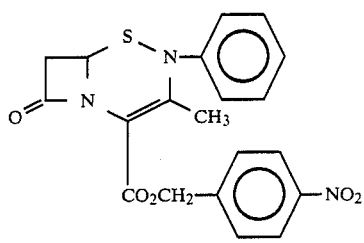

To a vigorously stirred solution of 1.59 g of 4'-nitrobenzyl-2-[4R-(2-benzthiazolyldithio)-2-oxo-1-azetidinyl]-3-anilino crotonate in 1000 ml dry benzene under an argon atmosphere was added 1.59 g of finely divided silver acetate. The solution was brought to reflux and stirring was continued until the reaction was shown by thin layer chromatography to be complete. The solution was then filtered through "Hyflo" and concentrated in vacuo. Chromatography on silica gel using hexane/ethyl acetate (1:1) as eluant afforded 0.76 g (62% of the theoretical yield) of 2-phenyl-4-(4-nitrobenzyloxycarbonyl)-6R-1-thia-2-azacephem as a colorless foam.

$\nu_{max}$ (film) 1782, 1715 cm$^{-1}$.

δ ppm (CDCl$_3$) 2.20 (3H, S, CH$_3$), 2.83 (1H, dd, Jab=16 Hz, Jax=2 Hz, J-7) 3.80 (1H, dd, Jab=16 Hz, Jbx=5 Hz, H-7) 4.50 (1H, dd, Jax=2 Hz, Jbx=5 Hz, H-6) 5.37 (2H, S, PhCH$_2$) 6.90–8.42 (9H, m, aromatics).

m/e Found 411.0880, C$_{20}$H$_{17}$N$_3$O$_5$S requires 411.0888.

(c) 1-Phenyl-(4-nitrobenzyloxycarbonyl)-azapenem

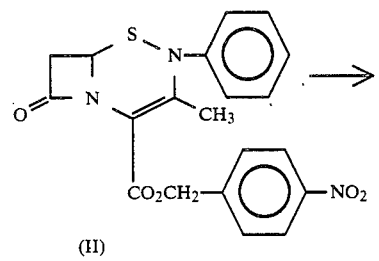

-continued

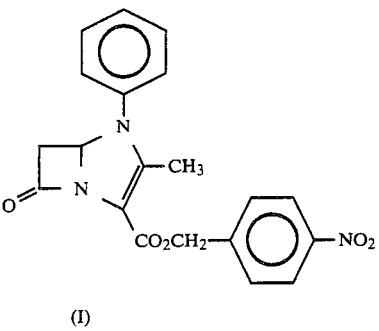

A solution of 0.674 g of 2-phenyl-4-(4-nitrobenzyloxycarbonyl)-6R-1-thia-2-azacephem in 15 ml dry acetonitrile was added rapidly to a vigorously stirred solution of 0.515 g of triphenylphosphine in 15 ml dry acetonitrile. The solution was then evaporated in vacuo to afford 1-phenyl-3-(4-nitrobenzyloxycarbonyl)-5ξ-azapenem as a yellow crystalline solid mixed with triphenylphosphine sulphide. The mixture was taken up in benzene, filtered and then washed with a further volume of benzene to afford 0.454 g of the pure phenyl azapenem. The mother liquors were concentrated in vacuo and chromatographed on silica gel eluting with ethyl acetate/hexane (1:1) to give a further 0.06 g of the phenyl azapenem. (Combined yield 0.516 g, 83% of the theoretical) mp 144.5°–145°,$\nu_{max}$ (CHCL$_3$) 1796, 1690 cm$^{-1}$ δ ppm (CDCl$_3$) 2.23 (3H, S, CH$_3$)3.30 (1H, dd, Jab=16 Hz, Jax=1 Hz, H-6), 3.76 (1H, dd, Jab=2.5 Hz, H-6), 5.21 (1H, d, Jab=14 Hz, CH$_2$Ph) 5.53 (1H, d, Jab=14 Hz, CH$_2$Ph), 5.68 (1H, dd, Jax=1 Hz, Jbx=2.5 Hz, H-5) 7.00–8.43 (9H, m, aromatics).

m/e Found 379.1186; C$_{20}$H$_{17}$N$_3$O$_5$ requires 379.1168.

EXAMPLE 3

(a)
4'-nitrobenzyl-2-[4R-ethylsulphenamoyl-2-oxo-1-azetidinyl]-3-methylsulphonyloxy crotonate

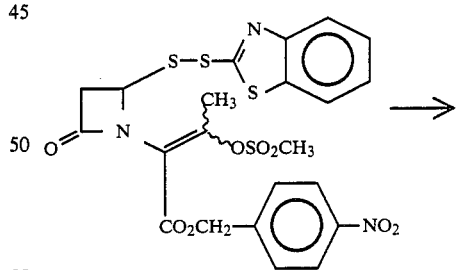

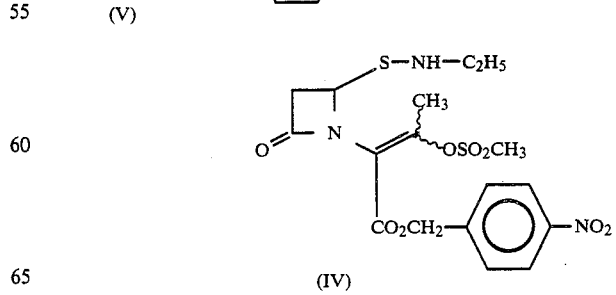

To a solution of 0.329 g of 4-nitrobenzyl-2-[4R-(2-benzthiazolyldithio)-2-oxo-1-azetidinyl]-3-methylsulphonyloxy crotonate in 4 ml dry chloroform was added 0.094 g silver acetate, followed by 37 μm ethylamine. When the reaction was shown by thin layer chromatography to be complete, the solution was filtered through "Hyflo", evaporated in vacuo, and chromatographed on silica gel, eluting with ethyl acetate/hexane (1:1). 0.194 g (75% of the theoretical yield), of 4'-nitrobenzyl-2-[4R-ethylsulphenamoyl-2-oxo-1-azetidinyl]-3-methylsulphonyloxy crotonate was obtained, as a mixture of E- and Z-isomers, as a pale yellow syrup.

Major isomer δ ppm (CDCl$_3$) 1.07 (3H, t, J=7.5 Hz, CH$_2$CH$_3$), 2.65 (3H, S, CH$_3$), 2.90 (2H, q, J=7.5 Hz, CH$_2$CH$_3$) 3.03–3.43 (2H, m, H-3), 3.30 (3H, S, SO$_2$CH$_3$), 5.00 (1H, t, J=4 Hz H-4), 5.38 (2H, s, CH$_2$P) 7.43–8.47 (4H, m, aromatics).

Minor isomer 1.07, (3H, t, J=7.5 Hz, CH$_2$CH$_3$) 2.37 (3H, S, CH$_3$), 2.90 (2H, q, J=7.5 Hz, CH$_2$CH$_3$) 3.03–3.43 (2H, m, H-3), 3.23 (3H, S, SO$_2$CH$_3$), 5.03 (1H, t, J=4 Hz, H-4), 5.38 (2h, S, CH$_2$Ph) 7.43–8.47 (4H, m, aromatics).

(b)
2-Ethyl-4-(4-nitrobenzyloxycarbonyl)-1-thia-2-azacephem.

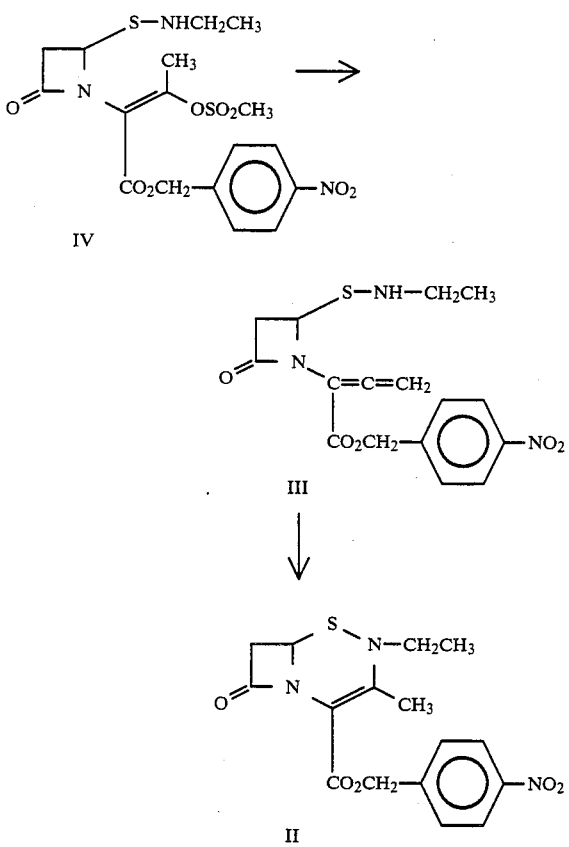

A solution of 0.065 g of 4'-nitrobenzyl-2-[4R-ethylsulphenamoyl-2-oxo-1-azetidinyl]-3-methylsulphonyloxy crotonate in 0.4 ml of deuteriochloroform was treated with a solution of 0.016 g of diazabicyclo(2,2,2)octane in 0.1 ml deuteriochloroform and the course of the reaction was observed using n.m.r spectroscopy.

A singlet at (δ 5.68) corresponding to the allene of formula III shown above was observed to appear, to increase and then to decay with the simultaneous growth of absorption due to the aza cephem derivative of formula II indicated above.

When the reaction was shown by n.m.r. to be complete, the solution was concentrated in vacuo and chromatographed on silica gel using ethylacetate/hexane (1:1) as eluant to give 2-ethyl-4-(4-nitrobenzyloxycarbonyl)-6R-1-thia-2-azacephem (0.012 g, 33% of the theoretical yield). This compound was identified by comparison with an authentic sample and converted to 1-ethyl-3-(4-nitrobenzyloxycarbonyl)-5ξ-azepenem as described in Example 1(c).

EXAMPLE 4

(a)

Phthalidyl-2-[4-(2-benzthiazolyldithio)-2-oxo-1-azetidinyl]-3-ethylamino crotonate

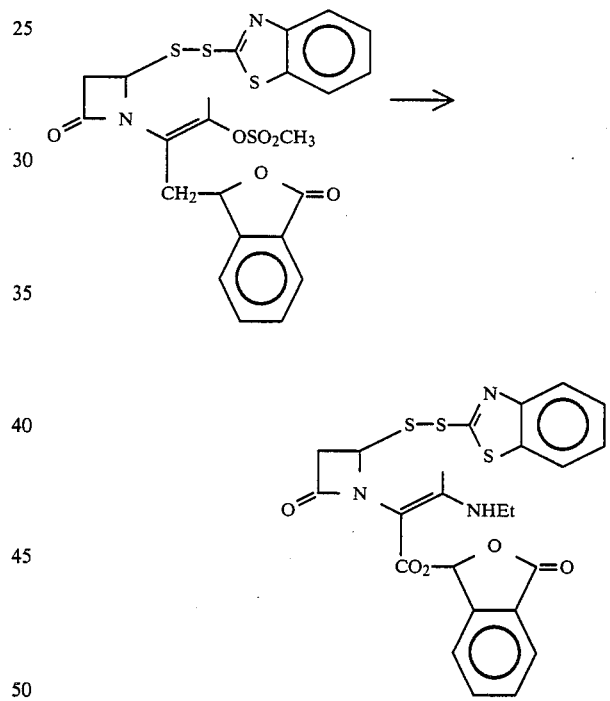

1.18 g of ethylamine was added dropwise to a solution of 6.90 g of phthalidyl 2-[4-(2-benzthiazolyldithio)-2-oxo-1-azetidinyl]-3-methylsulphonyl crotonate in 100 ml of dry dichloromethane at −20°. When the reaction was complete, the reaction mixture was filtered through Hyflo, evaporated in vacuo and chromatographed on silica gel, eluting with ethyl acetate/hexane, to give 3.4 g of the title compound as a mixture of isomers.

ν (film) 1780, 1670, 1590 cm$^{-1}$

δ (CDCl$_3$) 1.23 (t, J=7 Hz, 3H, CH$_2$CH$_3$), 1.95–2.16 (m, 3H, CH$_3$), 2.60–3.86 (m, 4H, CH$_2$CH$_3$, H$_3$), 4.86–5.16 (m, 1H, H$_4$) 7.06–8.00 (M, 9H, Phthalidyl CH, Aromatics) 9.06 (bs, 1H, NH).

(b)

2-Ethyl-4-phthalidyloxycarbonyl-1-thia-2-azacephem

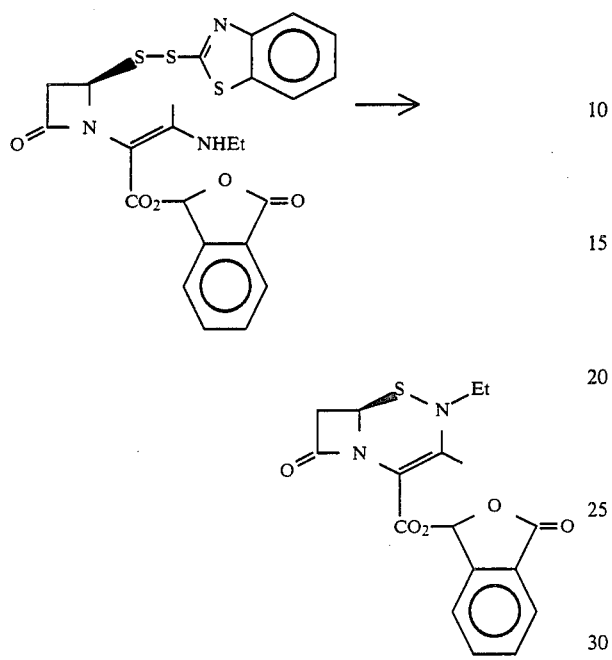

To a solution of 3.4 g of phthalidyl-2-[4-(2-benzthiazolyldithio)-2-oxo-1-azetidinyl]-3-ethylamino crotonate in 3000 ml of purified benzene under an argon atmosphere, was added 3.4 g of silver acetate. The solution was stirred rapidly and refluxed. When the reaction was complete, the solution was filtered through "Hyflo" and evaporated in vacuo. Chromatography on silica gel gave the title compound (phthalidyl 4-ethyl-3-methyl-8-oxo-5,4,1-thiadiazodicyclo[4,2,0]oct-2-ene-2-carboxylate) as two optically pure isomers in nonequivalent yield. Less polar isomer (0.38 g).

m.p. 174.5°–175°

$\nu$ (film) 1780, 1712 cm$^{-1}$ $[\alpha]_D$ CHCl$_3$ −358°

$\delta$ CDCl$_3$ 1.17 (t, J=7 Hz, 3H, CH$_3$CH$_2$) 2.46 (S, 3H, CH$_3$), 2.66 (dd, Jab=16 Hz, Jax=2 Hz, 1H, H$_7$), 3.60 (dd, Jab=16 Hz, Jbx=5 Hz, 1H, H$_7$), 3.0-4.0 (m, 2H, CH$_2$CH$_3$) 4.33 (dd, Jxa=2 Hz, Jxb=5 Hz, 1H, H$_6$) 7.43 (s, 1H, Phthalidyl CH) 7.33-8.10 (m, 4H, Aromatics).

The more polar isomer (0.213 g)

m.p. 165°–166°.

$\nu$ (film) 1780, 1712 cm$^{-1}$ $[\alpha]_D$ CHCl$_3$ −289°

$\delta$ (CDCl$_3$) 1.15 (t-J=7 Hz, 3H, CH$_2$CH$_3$) 2.36 (S, 3H, CH$_3$), 2.67 (dd, Jab=15 Hz, Jax=2 Hz, 1H, H$_7$), 3.08-4.00 (M, 3H, H$_7$, CH$_2$CH$_3$) 4.33 (dd, Jxa=2 Hz, Jxb=5 Hx, 1H, H$_6$), 7.20-8.06 (M, 5H, Phthalidyl CH, Aromatics).

(c) 1-Ethyl-3-phthalidyloxycarbonyl-azapenem

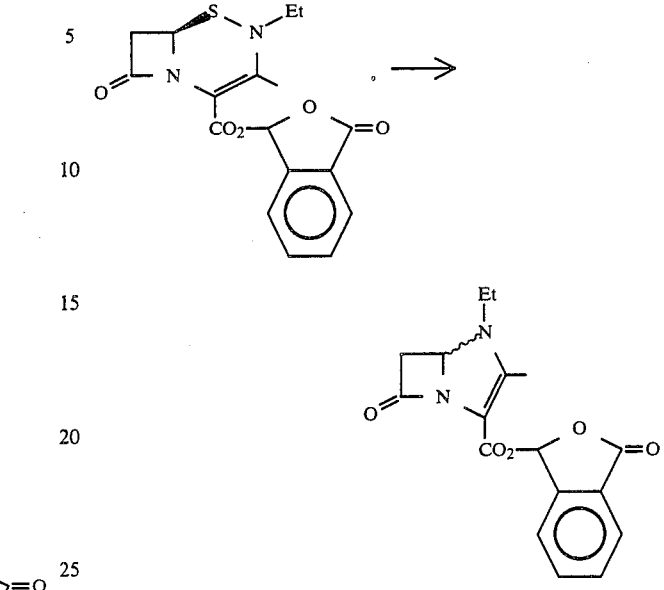

(i) To a solution of 0.326 g of triphenylphosphine in 10 ml of dry acetonitrile was added a solution of 0.374 g of the less polar isomer of 2-ethyl-4-phthalidyloxycarbonyl-1-thia-2-azecephem in 10 ml of dry acetonitrile. The reaction mixture was evaporated in vacuo, then chromatographed on silica gel eluting with ethyl acetate/hexane mixtures, to give the title compound (phthalidyl 4-ethyl-3-methyl-7-oxo-1,4-diazabicyclo[3,2,0]hept-2-ene-2-carboxylate) as two optically pure (5R) and (5S) isomers.

Less polar solvent (0.117 g)

m.p. 142.5° (Decomposition)

$\nu$ (CHCl$_3$) 1790, 1700 cm$^{-1}$ $[\alpha]_D$ (CHCl$_3$) +5.7°

$\delta$ (CDCl$_3$) 1.20 (t, J=7 Hz, 3H, CH$_2$CH$_3$) 2.33 (S, 3H, CH$_3$). 3.16 (dd, Jab=16 Hz, Jax=1.1 Hz, 1H, H$_6$) 2.89-3.62 (M, 2H, CH, CH$_3$) 3.69 (dd, Jab=16 Hz, Jbx=2.6 Hz, 1H, H$_6$), 5.21 (dd, Jxa−1.1 Hz, Jxb=2.6 Hz, 1H, H$_5$) 7.12-8.00 (M, 5H, Phthalidyl CH and Aromatics).

More polar isomer (0.070 g)

$\nu$ (film) 1785, 1690 cm$^{-1}$ $\delta$ (CDCl$_3$) 1.20 (t, J=7 Hz, 3H, CH$_2$CH$_3$), 2.21 (S, 3H, CH$_3$) 2.75-3.70 (M, 3H, H$_6$, CH$_2$CH$_3$), 3.71 (dd, Jab=16 Hz, Jbx=2.7 Hz, 1H, H$_6$), 5.23 (dd, Jxa=1.1 Hz, Jxb=2.75 Hz, 1H, H$_5$), 7.30 (S, 1H, Phthalidyl CH), 7.36-8.06 (M, 4H, Aromatics).

(ii) 0.188 g of the more polar product of Example 4b was reacted as described above, giving the title compound in the form of two optically pure isomers. Less polar isomer (0.0517 g)

m.p. 142°–142.5°

$\nu$ (film) 1785, 1692 cm$^{-1}$ $[\alpha]_D$ (CHCl$_3$) +4.5°

$\delta$ (CDCl$_3$) 1.20 (t, J=7 Hz, 3H, CH$_2$CH$_3$) 2.33 (S, 3H, CH$_3$) 2.81-3.75 (M, 3H, H$_6$, CH$_2$CH$_3$), 3.71 (dd, Jab=17 Hz, Jbx=2.7 Hz, 1H, H$_6$) 5.28 (dd, Jxa=1.1 Hz, Jxb=2.7 Hz, 1H, H$_5$) 7.26-8.10 (M, 5H, Phthalidyl CH, Aromatics).

More polar isomer (0.102 g)

m.p. 126° (Decomposition)

$\nu$ (film) 1785, 1690 cm$^{-1}$

[α]$_D$ (CHCl$_3$) +203°

δ (CDCl$_3$) 1.216 (t, J=7 Hz, 3H, CH$_2$CH$_3$), 2.25 (S, 3H, CH$_3$) 2.80–3.70 (M, 3H, H$_6$, CH$_2$CH$_3$) 3.75 (dd, Jba=16 Hz, Jbx=2.7 Hz, 1H, H$_6$), 5.24 (dd, Jxa=1.1 Hz, Jxb=2.7 Hz, 1H, H$_5$) 7.26–8.10 (M, 5H, Phthalidyl CH, Aromatics).

EXAMPLE 5

(a) Phthalidyl 2-[4-(2-benzthiazolyldithio)-2-oxo-1-azetidinyl]-3-phenylamino crotonate

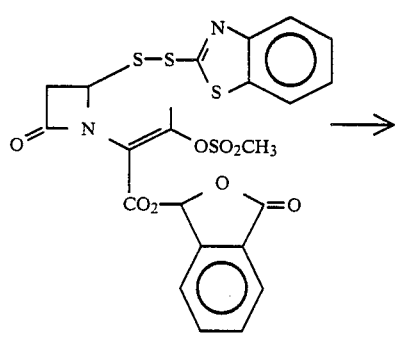

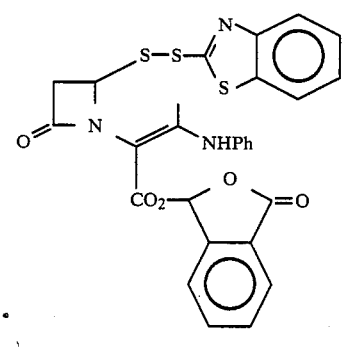

To a solution of 5.6 g of phthalidyl-2-[4-(2-benzthiazolyldithio)-2-oxo-1-azetidinyl]-3-methylsulphonyl crotonate in 50 ml of dichloromethane was added 1.76 g of aniline followed by a solution of 1.08 g of dabco [diazabicyclo(2,2,2)octane] in 10 ml of dichloromethane. The reaction mixture was stirred for 30 minutes, then diluted with dichloromethane, washed with water, dilute hydrochloric acid (0.5M) and water, dried and evaporated in vacuo. The residue was chromatographed on silica gel, eluting with ethyl acetate/hexane mixtures to give 4.5 g of the title compound as a light brown foam.

ν (film) 1780, 1670 cm$^{-1}$

δ (CDCl$_3$) 2.13 (S, 3H, CH$_3$), 2.90–3.48 (M, 2H, H$_3$), 4.96–5.20 (m, 1H, H$_4$) 6.83–8.05 (M, 14H, Phthalidyl CH, Aromatics) 10.76 (S, 1H, NHPh).

(b) 2-Phenyl-4-phthalidyloxycarbonyl-1-thia-2-azacephem

To a solution of 4.5 g of phthalidyl 2-[4-(2-benzthiazolyldithio)-2-oxo-1-azetidinyl] 3-phenylamino crotonate in 2000 mls of purified benzene was added 4.5 g of finely divided silver acetate. The reaction and purification were carried out as described in Example 4b. The title compound (phthalidyl 3-methyl-8-oxo-4-phenyl-5,4,1-triazabicyclo[4,2,0]oct-2-ene-2-carboxylate) was obtained in the form of two optically pure isomers.

Less polar isomer
m.p. 177°–178°
ν (CHCl$_3$) 1780, 1726 cm$^{-1}$
δ (CDCl$_3$) 2.28 (S, 3H, CH$_3$) 2.81 (dd, Jab=16 Hz, Jax=2 Hz, 1H, H$_7$), 3.76 (dd, Jba=16 Hz, Jbx=6 Hz, 1H, H$_7$) 4.48 (dd, Jxa=2 Hz, Jxb=5 hz, 1H, H$_6$) 6.90–8.06 (M, 10H, Phthalidyl CH, Aromatics).

More polar isomer
ν (film) 1782, 1727 cm$^{-1}$
[α]$_D$ (CHCl$_3$) −200.50°
δ (CDCl$_3$) 2.15 (S, 3H, CH$_3$) 2.83 (dd, Jab=16 Hz, Jax=2 Hz, 1H, H$_7$) 3.79 (dd, Jba=16 Hz, Jbx=5 Hz, 1H, H$_7$) 4.47 (dd, Jxa=2 Hz, Jxb=5 Hz, 1H, H$_6$) 6.90–8.06 (M, 10H, Phthalidyl CH, Aromatics).

(c) 1-Phenyl-3-phthalidyloxycarbonyl-azapenem

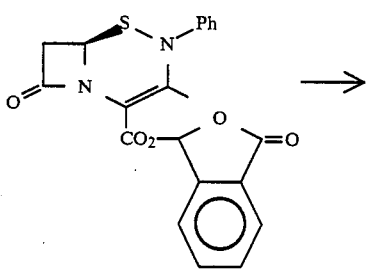

-continued

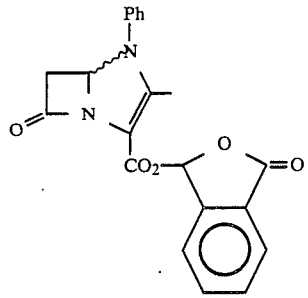

(i) To a solution of 0.07 g of triphenylphosphine in 3 ml of dry acetonitrile was added a solution of 0.10 g of the less polar isomer of 2-phenyl-4-phthalidyloxycarbonyl-1-thia-2-azacephem in 2 ml of dry acetonitrile. The resulting pale yellow solution was evaporated immediately in vacuo, then taken up in toluene and chromatographed on silica gel, eluting with ethyl acetate/hexane mixtures to give the title compund (phthalidyl 3-methyl-7-oxo-4-phenyl-1,4-diazabicyclo[3,2,0]hept-2-ene-2-carboxylate) as two optically pure (5R) and (5S) isomers. Less polar isomer (0.054 g)

m.p. 125.5°–129.5°

$\nu$ (film) 1790, 1700 cm$^{-1}$ $[\alpha]_D$ (CHCl$_3$) +84.6°

$\delta$ (CDCl$_3$) 2.26 (S, 3H, CH$_3$), 3.26 (d,d, Jab=16 Hz, Jax=1.5 Hz, 1H, H$_6$), 3.70 (dd, Jba=16 Hz, Jbx=2.5 Hz, 1H, H$_6$), 5.66 (dd, Jax=1.5 Hz, Jxb=2.5 Hz, 1H, H$_5$), 6.96–8.06 (M, 10H, Phthalidyl, CH, Aromatics)

More polar isomer (0.0196 g)

m.p. 145°–146°

$\nu$ (film) 1788, 1695 cm$^{-1}$ $[\alpha]_D$ (CHCl$_3$) −274.7°

$\delta$ (CDCl$_3$) 2.15 (S, 3H, CH$_3$), 3.28 (dd, Jab=16 Hz, Jax=1.5 Hz, 1H, H$_6$) 3.73 (dd, Jba=16 Hz, Jbx=2.5 Hz, 1H, H), 5.66 (dd, Jxa=1.5 Hz, Jxb=2.5 Hz, 1H, H$_5$), 7.03–8.13 (M, 10H, Phthalidyl CH, Aromatics).

(ii) 0.1 g of the more polar product of Example 5b was reacted as described above, also giving two isomers.

Less polar isomer (0.036 g)

$\nu$ (film) 1790, 1700 cm$^{-1}$ $\delta$ (CDCl$_3$) 2.23 (S, 3H, CH$_3$), 3.25 (dd, Jab=16 Hz, Jax=1.5 Hz, 1H, H$_6$), 3.66 (dd, Jba=16 Hz, Jbx=2.5 Hz, 1H, H$_6$), 5.60 (dd, Jax−1.5 Hz, Jxb=2.5 Hz, 1H, H$_5$), 6.93–8.03 (M, 10H, Phthalidyl CH, Aromatics).

More polar isomer (0.0486 g)

m.p. 139°–141°

$\nu$ (film) 1790, 1700 cm$^{-1}$ $[\alpha]_D$ (CHCl$_3$) +302.7°

$\delta$ (CDCl$_3$) 2.13 (S, 3H, CH$_3$) 3.06 (dd, Jab=16 Hz, Jax=1.5 Hz, 1H, H$_6$) 3.70 (dd, Jba=16 Hz, Jbx=2.5 Hz, 1H, H$_6$), 5.60 (dd, Jxa=1.5 Hz, Jxb=2.5 Hz, 1H, H$_5$), 6.96–8.03 (M, 10H, Phthalidyl CH, Aromatics).

EXAMPLE 6

(a) Phthalidyl 2-[4-(2-benzthiazolyldithiio)-2-oxo-1-azetidinyl]-3-cyanomethyl crotonate

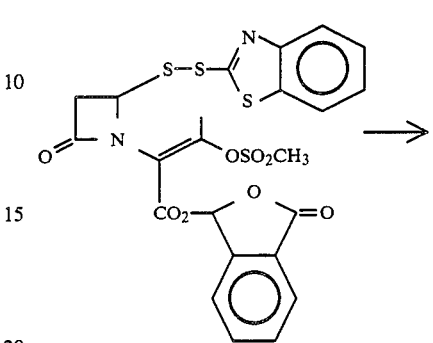

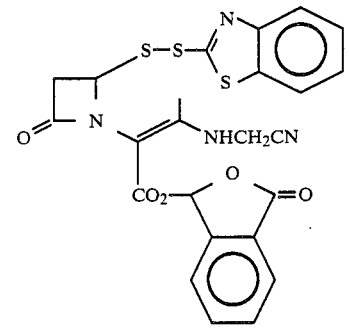

To a suspension of 0.154 g of cyanomethylamine hydrochloride in 10 ml of dry dichloromethane was added 0.33 g of triethylamine. When the solution became homogeneous, a solution of 0.96 g phthalidyl-2-[4-(2-benzthiazolyldithio)-2-oxo-1-azetidinyl]-3-methylsulphonyl crotonate in 8 ml of dichloromethane was added in one batch. The reaction was carried out and the mixture worked up as described in Example 5a, giving 0.7 g of the title compound.

$\nu$ (film) 1780, 1680 cm$^{-1}$ $\delta$ (CDCl$_3$) 2.26 (S, 3H, CH$_3$), 2.73–3.90 (M, 2H, H$_3$), 4.24 (d, J=6 Hz, 2H, CH$_2$CN), 4.96–5.23 (M, 1H, H$_4$) 7.16–8.10 (M, 5H, Phthalidyl CH, Aromatics). 9.06–9.56 (M, 1H, NH).

(b) 2-Cyanomethyl-4-phthalidyloxycarbonyl-1-thia-2-azacephem

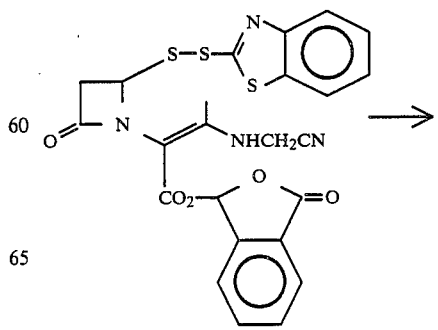

-continued

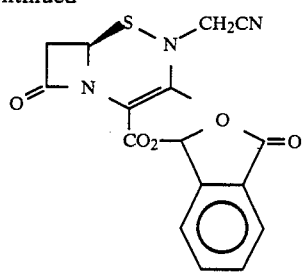

To a solution of 0.323 g of cyanomethyl enamine in 150 ml of purified benzene, held under an argon atmosphere, was added 0.323 g of silver acetate. The reaction and purification were carried out as described in Example 4(b), giving the title compound (phthalidyl 4-cyanomethyl-8-oxo-5,4,1-thiadiazabicyclo[4,2,0]oct-2-ene-2-carboxylate) as two optically pure isomers.

Less polar isomer (0.083 g)
m.p. 201° DEC
$\nu$ (film) 1783, 1731 cm$^{-1}$
$\delta$ (CDCl$_3$) 2.46 (S, 3H, CH$_3$), 2.80 (dd, Jab=16 Hz, Jax=2 Hz, 1H, H$_7$) 3.79 (dd, Jba=16 Hz, Jbx=4.5 Hz, 1H, H$_7$) 4.06 (d, Jab=18.6 Hz, 1H, CH$_2$CN), 4.62 (d, Jba=18.6 Hz, CH$_2$CN), 4.75 (dd, Jxa=2 Hz, Jxb=4.5 Hz, 1H, H$_6$), 7.23-8.06 (M, 5H, Phthalidyl CH, Aromatics).

More polar isomer (0.075 g)
$\nu$ (film) 1783, 1730 cm$^{-1}$
$\delta$ (CDCl$_3$) 2.36 (S, 3H, CH$_3$), 2.76 (dd, Jab=16 Hz, Jax=2 Hz, 1H, H$_7$) 3.79 (dd, Jba=16 Hz, Jbx=5 Hz, 1H, H$_7$) 4.03 (d, Jab=18 Hz, 1H, CH$_2$CN), 4.57 (d, Jba=18 Hz, 1H, CH$_2$CN) 4.74 (dd, Jxa=2 Hx, Jxb=5 Hz, 1H, H$_6$), 7.20-8.00 (M, 5H, Phthalidyl CH, Aromatics).

(c) 1-Cyanomethyl-3-phthalidyloxycarbonyl-1-azapenem

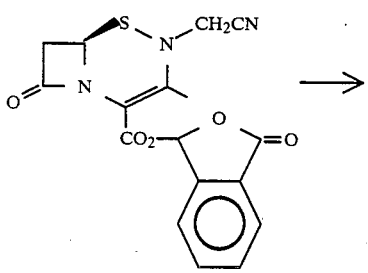

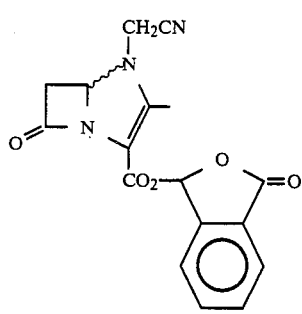

To a solution of 0.11 g of triphenylphosphine in 5 ml of dry acetonitrile was added a solution of 0.131 g of the less polar isomer of 2-cyanomethyl-4-phtalidyloxycarbonyl-1-thia-2-azacephem in 6 ml of acetonitrile. The reaction mixture was evaporated in vacuo and chromatographed on silica gel, eluting with ethyl acetate/hexane and ethyl acetate/dichloromethane mixtures to give the title compound (phthalidyl 4-cyanomethyl-3-methyl-7-oxo-1,4-diazabicyclo[3,2,0]hept-2-ene-2-carboxylate) as two optically pure isomers.

Less polar isomer (0.06 g) mp. 157°-158°
$\nu$ (CH$_3$CN) 1792, 1711, 1588 cm.$^{-1}$
$\delta$ (CD$_3$CN) 2.30 (S, 3H, CH$_3$), 3.28 (dd, Jab=17 Hz, Jax=1.2 Hz, H6), 3.76 (dd, Jba=17 Hz, Jbx=2.5 Hz, H6), 4.26 (S, 2H, CH$_2$CN), 5.28 (dd, Jxa=1.2 Hz, Jxb=2.5 Hz, Hz), 7.30-8.0 (m, 5H,aromatics, phthalidyl-CH).

More polar isomer (0.023 g) mp. 156°-157°
$\nu$ (CH$_3$CN) 1792, 1711, 1588 cm$^{-1}$
$\delta$ (CD$_3$CN) 2.25 (S, 3H, CH$_3$), 3.26 (dd, Jab=16 Hz, Jax=1.2 Hz, H6), 3.73 (dd, Jba=16 Hz, Jbx=2.5 Hz, H6), 4.23 (S, 2H, CH$_2$CN), 5.28 (dd, Jxa=1.2 Hz, Jxb=2.5 Hz), 7.30-8.0 (m, 5H, aromatics, phthalidyl-CH)

EXAMPLE 7

(a) Phthalidyl 2-[4-(2-benzithiazolylditho)-2-oxo-1-azetidinyl]-3-(4-cyanophenyl) crotonate

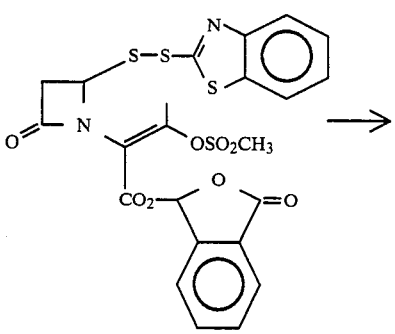

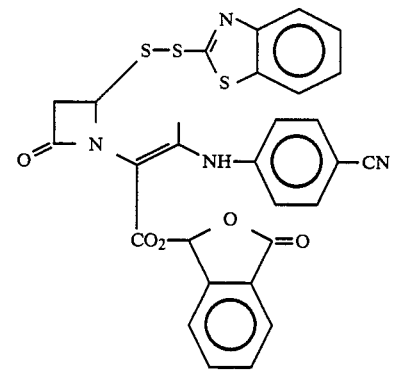

To a solution of 1.5 g of phthalidyl 2-[4-(2-benzthiazolyldithio)-2-oxo-1-azetidinyl]-3-methylsulphonyl crotonate in 10 ml of dry dichloromethane was added 0.614 g of aminobenzonitrile followed by 0.313 g of triethylamine. The solution was stirred for 0.5 hour, then diluted and washed with water and brine, dried, and evaporated in vacuo. The residue was chromatographed on silica gel eluting with ethyl acetate/hexane to give 0.78 g of the title compound.
$\nu$ (film) 1781, 1676 cm$^{-1}$
$\delta$ (CDCl$_3$) 2.23 (S, 3H, CH$_3$), 2.73-3.60 (M, 2H, H$_3$), 5.06-5.33 (M, 1H, H$_4$), 6.90-8.13 (M, 9H, Phthalidyl CH, Aromatics), 11.03 (d, J=3H, 1H, NH).

(b) 2-(4-Cyanophenyl)-4-phthalidyloxycarbonyl-1-thia-2-azacephem

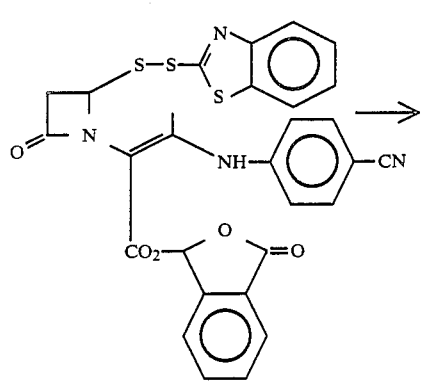

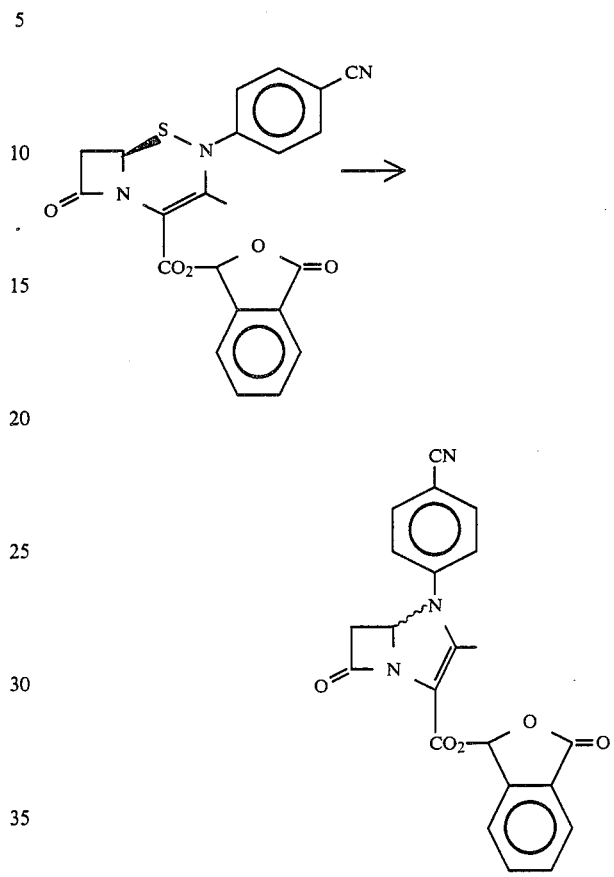

(c) 1-(4-Cyanophenyl)-3-phthalidyloxycarbonyl-1-aza penem

To a solution of 0.78 g of 4-cyanophenyl enamine in 300 ml of purified benzene, held under an argon atmosphere, was added 0.78 g of silver acetate. The reaction and purification were carried out as described in Example 4b, giving the title compound (phthalidyl-4-(4-cyanophenyl)-3-methyl-8-oxo-5,4,1-thiadiazabicyclo[4,2,0]oct-2-ene-2-carboxylate) in the form of two optically pure isomers.

Less polar isomer (0.199 g)

$\nu$ (film) 1785, 1735 cm$^{-1}$ $\delta$ (CDCl$_3$) 2.31 (S, 3H, CH$_3$), 2.92 (dd, J=16 Hz, Jxa=2.5 Hz, 1H, H$_7$), 3.78 (dd, Jba=16 Hz, Jbx=5 Hz, 1H, H$_7$) 4.48 (dd, Jxa=2.5 Hz, Jxb=5 Hz, 1H, H$_6$), 7.03-8.03 (M, 9H, Phthalidyl CH, Aromatics).

More polar isomer (0.14 g)

$\nu$ (film) 1795, 1730 cm$^{-1}$ $\delta$ (CDCl$_3$) 2.20 (S, 3H, CH$_3$), 2.90 (dd, Jab=16 Hz, Jax=2 Hz, 1H, H$_7$), 3.80 (dd, Jba=16 Hz, Jbx=5 Hz, 1H, H$_7$), 4.50 (dd, Jxa=2 Hz, Jxb=5 Hz, 1H, H$_6$), 6.96-8.10 (M,9H, Phthalidyl CH, Aromatics).

To a solution of 0.144 g of triphenylphosphine in 8 ml of dry acetonitrile was added a solution of the less polar isomer of 2-(4-cyanophenyl)-4-phthalidyloxycarbonyl-1-thia-2-azacephem. The solution was evaporated in vacuo and the residue was chromatographed on silica gel, eluting with ethyl acetate/hexane to give the title compound (phthalidyl 4-(4-cyanophenyl)-3-methyl-7-oxo-1,4-diazabicyclo[3,2,0]hept-2-ene-2-carboxylate) as two optically pure isomers.

Less polar isomer (0.1 g)

$\nu$ (film) 1790, 1708 cm$^{-1}$ $\delta$ (CDCl$_3$) 2.47 (S, 3H, CH$_3$), 3.30 (dd, Jab=16 Hz, Jax=1 Hz, 1H, H$_6$), 3.83 (dd, Jba=16 Hz, Jbx=2.5 Hz, 1H, H$_6$), 5.84 (dd, Jxa=1 Hz, Jxb=2.5 Hz, 1H, H$_5$) 7.10-8.06 (M, 9H, Phthalidyl CH, Aromatics).

More polar isomer (0.043 g)

$\nu$ (film) 17$\pi$, 1706 cm$^{-1}$ $\delta$ (CDCl$_3$) 2.35 (S, 3H, CH$_3$) 3.30 (dd, Jab=16 Hz, Jax=1 Hz, 1H, H$_6$), 3.81 (dd, Jba=16 Hz, Jbx=2.5 Hz, 1H, H$_6$) 5.83 (dd, Jxa=1 Hz, Jxb=2.5 Hz, 1H, H$_5$) 7.00-8.06 (M, 9H, Phthalidyl CH, Aromatics).

EXAMPLE 8

(a) Phthalidyl 3,3-dimethyl-7-oxo-4,1-thiazabicyclo[3,2,0]heptan-2-carboxylate

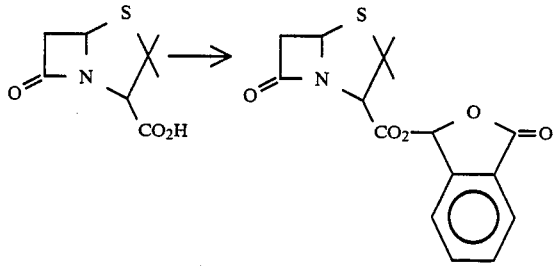

To a solution of 7.4 g of penicillanic acid (3,3-dimethyl-7-oxo-4,1-thiazabicyclo[3,2,0]heptan-2-carboxylate) in 30 ml of dimethylacetamide was added 5.53 ml of diisopropylamine. After 5 minutes 8.4 g of phthalidyl bromide were added and the reaction mixture was stirred until the reaction was shown to be complete by thin layer chromatography. The solution was diluted with ethyl acetate and washed six times with water, then dried and evaporated to afford the title compound in crude form as a dark oil. Chromatography over silica gel, eluting with ethyl acetate/hexane mixtures gave the title compound (9.11 g, 74%) as a mixture of phthalidyl isomers which could be partially separated by crystallization.

Crystalline isomer.
m.p. 165°–166°
$\nu$ (CHCl$_3$) 1785 (shoulders at 1792 and 1775) cm$^{-1}$.
$\delta$ (CDCl$_3$) 1.56 (S, 3H, CH$_3$), 1.67 (S, 3H, CH$_3$), 3.03 (dd, Jax=2 Hz, Jab=16 Hz, 1H, H$_6$), 3.60 (dd, Jbx=4 Hz, Jba=16 Hz, 1H, H$_6$) 4.56 (S, 1H, H$_3$), 5.26 (dd, Jxa=2Hz, Jxb=4 Hz, 1H, H$_5$), 7.50 (S, 1H, Phthalidyl C<u>H</u>) 7.50–8.20 (M, 4H, Aromatics).

Second isomer (by subtraction)
$\nu$ (film) 1785 (shoulder 1792 and 1775) cm$^{-1}$
$\delta$ (CDCl$_3$) 1.58 (S, 3H, CH$_3$), 1.63 (S, 3H, CH$_3$), 3.03 (dd, Jab=16 Hz, Jax=2.5 Hz, 1H, H$_6$), 3.62 (dd, Jba=16 Hz, Jbx=4 Hz, 1H, H$_6$), 4.56 (S, 1H, H$_3$), 5.23 (dd, Jxa=2 Hz, Jxb=4 Hz, 1H, H$_5$), 7.46 (S, 1H, Phthalidyl C<u>H</u>), 7.50–8.2 (M, 4H, Aromatics).

(b) Phthalidyl 3,3-dimethyl-4,7-dioxo-4,1-thiazabicyclo[3,2,0]heptan-2-carboxylate

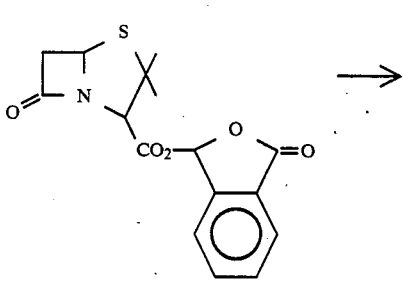

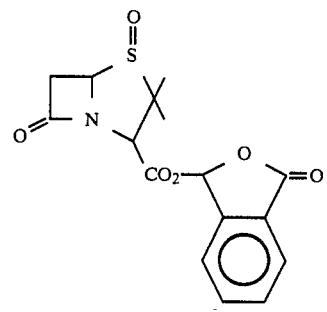

A solution of 9.0 g of phthalidyl 3,3-dimethyl-7-oxo-4,1-thiazabicyclo[3,2,0]heptan-2-carboxylate in 100 ml of acetic acid was cooled to 0° and to it was added dropwise a solution of 5.8 g of m-chloroperbenzoic acid in 55 ml of ethyl acetate. The reaction was monitored using thin layer chromatography. The resulting gelatinous solution was diluted with chloroform (300 ml), washed with saturated aqueous sodium bicarbonate (400 ml), dried over magnesium sulphate and evaporated in vacuo to give the mixed sulphoxides as a gelatinous solid. A sample of the crude product was chromatographed on silica gel, eluting with ethyl acetate/hexane mixtures. The less polar isomer was obtained as an oil, and the more polar isomer as a gelatinous solid.

Less polar isomer $\nu$ (film) 1788 cm$^{-1}$
$\delta$ (CDCl$_3$) 1.35 (S, 3H, CH$_3$), 1.63 (S, 3H, CH$_3$), 3.40 (d, J=4 Hz, 2H, H$_6$) 4.63 (S, 1H, H$_3$), 5.06 (t, J=4 Hz, 1H, H$_3$), 7.56 (S, 1H, Phthalidyl C<u>H</u>) 7.50–8.23 (M, 4H, Aromatics).

More polar isomer
$\nu$ (film) 1788 cm$^{-1}$
$\delta$ (CDCN) 1.33 (S, 3H, CH$_3$), 1.61 (S, 3H, CH$_3$), 3.08 (dd, Jab=16 Hz, Jax=2 Hz, 1H, H$_6$), 3.44 (dd, Jba=16 Hz, Jbx=4 Hz, 1H, H$_6$), 4.50 (S, 1H, H$_3$), 5.10 (dd, Jax=2 Hz, Jbx=4 Hz, 1H, H$_5$), 7.48 (S, 1H, Phthalidyl C<u>H</u>), 7.55–8.13 (M, 4H, Aromatics).

(c) Phthalidyl 2-[4-(benzthiazolyldithio)-2-oxo-1-azetidinyl]-2-(1-propen-2-yl)-acetate

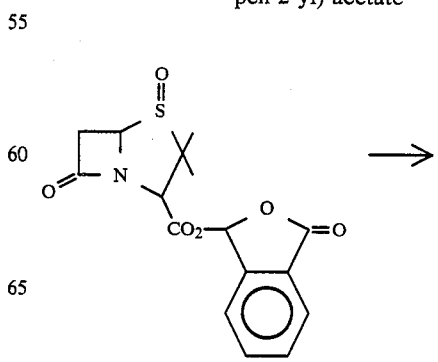

-continued

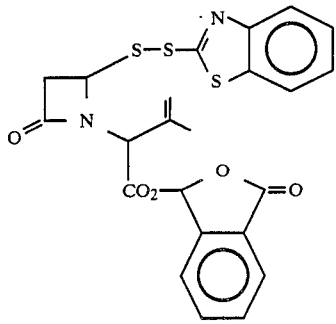

To a solution of 8.1 g of crude phthalidyl 3,3-dimethyl-4,7-dioxo-4,1-thiazabicyclo[3,2,0]heptan-2-carboxylate in 200 ml of dry toluene was added 3.83 g of mercaptobenzthiazole. The solution was refluxed until all the starting material had been consumed, then cooled, and washed twice with sodium bicarbonate and once with water, dried and evaporated in vacuo to give the title compound (14 g). An aliquot was chromatographed on silica gel eluting with ethyl acetate/hexane mixtures to afford the title compound as a colorless foam.

ν (CHCl$_3$) 1780, (shoulder at 1770) cm$^{-1}$

δ (CDCl$_3$) 1.92 (S, 3H, CH$_3$), 2.96–3.73 (m, 2H, H$_3$) 4.90 (d, J=4 Hz, H$_3$) 5.00–5.43 (M, 3H, H$_4$=CH$_2$) 7.10–8.10 (M, 9H, Phthalidyl, Aromatics).

(d) Phthalidyl 2-[4-(2-benzthiazolyldithio)-2-oxo-1-zaetidinyl]-3-hydroxy crotonate

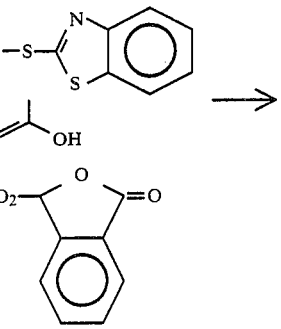

Ozone was bubbled through a solution of 149 of crude phthalidyl 2-[4-(2-benzthiazolyldithio)-2-oxo-1-azetidinyl]-2-(1-propen-2-yl)-acetate in a mixture of 200 ml of dichloromethane and 65 ml of methanol cooled to −78°. When the starting material had been consumed, the reaction was quenched by the addition of dimethyl sulphide (30 ml) in one batch. The reaction was warmed to room temperature and evaporated in vacuo. The residue was dissolved in ethyl acetate, washed twice with water and twice with brine, then dried (MgSO$_4$) and evaporated to yield the title compound as a colorless foam. (10.2 g)

ν (film) 1788, 1675 cm$^{-1}$

δ (CDCl$_3$) 2.18 (S, 3H, CH$_3$), 3.05–3.55 (m, 2H, H$_3$), 5.0–5.30 (M, 1H, H$_4$), 7.2–8.06 (m, 9H, Phthalidyl C$\underline{H}$, Aromatics), 11.1 (bs, 1H, OH).

(e) Phthalidyl 2-[4-(2-benzthiazolyl)-2-oxo-1-azetidinyl]-3-O-methylsulphonyl crotonate

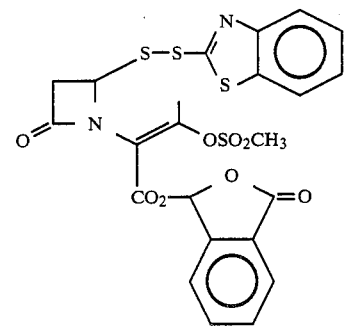

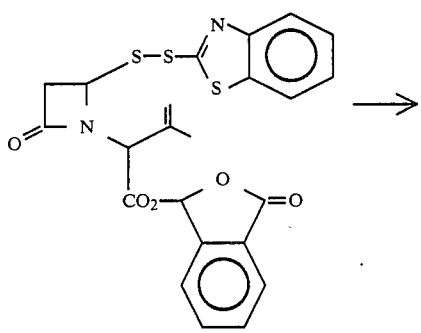

To a solution of 10.0 g of phthalidyl 2-[4-(2-benzthiazolyldithio)-2-oxo-1-azetidinyl]-3-hydroxy crotonate in 80 ml of dry dichloromethane, cooled to −20°, was added 2.018 g of triethylamine followed by 2.39 g of methanesulphonyl chloride. The reaction mixture was diluted with dichloromethane, and washed three times with water, then dried and evaporated in vacuo. The resulting oil was chromatographed on silica gel eluting with ethyl acetate/hexane mixtures to give the title product (5.6 g) as mixture of E and Z isomers.

ν (film) 1786 cm$^{-1}$

δ (CDCl$_3$) 2.48 and 2.52 (S, 3H, CH$_3$) 3.03–3.66 (m, 2H, H$_3$), 3.28 (S, 3H, C$\underline{H_3}$SO$_2$) 5.20–5.50 (m, 1H, H$_4$), 7.00–7.93 (m, 9H, Phthalidyl C$\underline{H}$, Aromatics).

What we claim is:

1. A penem compound of the formula

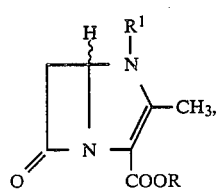

wherein

R is a carboxyl esterifying group removable by hydrolysis, reduction, or enzymatic action, or is a pharmaceutically acceptable cation; and $R^1$ is alkyl having 1 to 4 carbon atoms or such alkyl substituted by —CN or —COO($C_1$–$C_4$-alkyl), or is phenyl or phenyl mono- or di-substituted by the same or different substituents which are —CN, halogen, or —COO($C_1$–$C_4$-alkyl).

2. A compound as in claim 1 wherein R is phthalidyl and $R^1$ is ethyl.

3. A compound as in claim 1 wherein R is phthalidyl and $R^1$ is phenyl.

4. A compound as in claim 1 wherein R is phthalidyl and $R^1$ is cyanophenyl.

5. A compound as in claim 1 wherein R is p-nitrobenzyl and $R^1$ is phenyl.

6. A compound as in claim 1 wherein R is p-nitrobenzyl and $R^1$ is ethyl.

7. A compound as in claim 1 wherein R is hydrogen, p-nitrobenzyl, phthalidyl, or pivaloyloxymethyl.

8. A compound as in claim 1 wherein $R^1$ is cyanomethyl and R is phthalidyl.

9. A pharmaceutical composition comprising an antibacterially effective amount of a compound as in claim 1 together with a pharmaceutically acceptable carrier.

10. The method of treating a bacterial infection in a patient requiring such treatment, which method comprises orally or parenterally administering to said patient an antibacterially effective amount of a compound as in claim 1.

* * * * *